United States Patent
Bai et al.

(10) Patent No.: US 8,946,478 B2
(45) Date of Patent: Feb. 3, 2015

(54) BENZAMIDE DERIVATIVE WITH ANTICANCER ACTIVITY AND PREPARATION METHOD AND USE THEREOF

(75) Inventors: Hua Bai, Taizhou (CN); Xuyang Zhao, Chengdu (CN); Yongxiang Gong, Taizhou (CN); Jinqing Zhong, Taizhou (CN); Qifeng Zhu, Taizhou (CN); Xiaoyu Liu, Taizhou (CN); Lifei Liu, Taizhou (CN); Qixian Zhou, Taizhou (CN)

(73) Assignee: Zhejiang Hisun Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 13/883,520

(22) PCT Filed: Nov. 3, 2011

(86) PCT No.: PCT/CN2011/001854
§ 371 (c)(1),
(2), (4) Date: May 3, 2013

(87) PCT Pub. No.: WO2012/058866
PCT Pub. Date: May 10, 2012

(65) Prior Publication Data
US 2013/0225810 A1 Aug. 29, 2013

(30) Foreign Application Priority Data
Nov. 5, 2010 (CN) .......................... 2010 1 0532658

(51) Int. Cl.
| | | |
|---|---|---|
| C07C 255/60 | (2006.01) | |
| C07C 233/65 | (2006.01) | |
| C07D 295/192 | (2006.01) | |
| C07C 231/02 | (2006.01) | |
| C07C 233/92 | (2006.01) | |
| C07C 253/30 | (2006.01) | |
| C07C 255/57 | (2006.01) | |
| C07C 271/64 | (2006.01) | |

(52) U.S. Cl.
CPC ............. *C07C 255/60* (2013.01); *C07C 231/02* (2013.01); *C07C 233/65* (2013.01); *C07C 233/92* (2013.01); *C07C 253/30* (2013.01); *C07C 255/57* (2013.01); *C07C 271/64* (2013.01); *C07D 295/192* (2013.01)
USPC ............. 564/166; 564/134; 560/22; 558/415; 548/539; 546/226; 544/162

(58) Field of Classification Search
CPC . C07C 255/60; C07C 233/65; C07D 295/192
USPC ................... 564/134, 166; 560/22; 558/415; 548/539; 546/226; 544/162
See application file for complete search history.

(56) References Cited

U.S. PATENT DOCUMENTS

| 4,101,481 A | 7/1978 | Branlard et al. |
|---|---|---|
| 5,464,871 A | 11/1995 | Kun et al. |
| 5,731,351 A | 3/1998 | Gericke et al. |
| 8,389,766 B2 * | 3/2013 | Jung et al. ..................... 564/153 |
| 2009/0123419 A1 | 5/2009 | Sherman et al. |
| 2009/0131529 A1 | 5/2009 | Sherman et al. |
| 2009/0149397 A1 | 6/2009 | Ossovskaya et al. |

FOREIGN PATENT DOCUMENTS

| AU | 7670387 A | 2/1988 |
|---|---|---|
| CN | 1063438 C | 3/2001 |
| EP | 0 258 631 A2 | 3/1988 |
| EP | 0258631 A | 3/1988 |
| JP | 63-48257 A | 2/1988 |
| JP | 09124583 A | 5/1997 |
| WO | WO 2005019188 A1 | 3/2005 |

OTHER PUBLICATIONS

Wolff, Manfred E. "Burger's Medicinal Chemistry, 5ed, Part I", John Wiley & Sons, 1995, pp. 975-977.*
Banker (Modern Pharmaceutics) Banker, G.S. et al, "Modern Pharmaceutics, 3ed.", Marcel Dekker, New York, 1996, pp. 451 and 596.*
Japanese Office Action dated Sep. 3, 2014 from corresponding Japanese Application No. 2013-536983.
International Search Report dated Jan. 19, 2012 from corresponding International Application No. PCT/CN2011/001854.

* cited by examiner

*Primary Examiner* — Shailendra Kumar
(74) *Attorney, Agent, or Firm* — Wolf, Greenfield & Sacks, P.C.

(57) ABSTRACT

Provided are a benzamide derivative as shown in formula (I) or a pharmaceutically acceptable salt thereof, and the preparation method and use thereof for preparing a medicine for treating cancer, wherein the group definitions of formula (I) are as set out in the description.

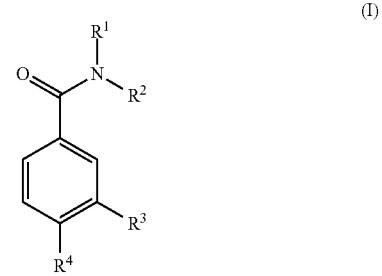

29 Claims, No Drawings

BENZAMIDE DERIVATIVE WITH ANTICANCER ACTIVITY AND PREPARATION METHOD AND USE THEREOF

This application is a 371 of PCT/CN11/01854 Nov. 3, 2011.

FIELD OF THE INVENTION

The present invention relates to benzamide derivatives with anti-cancer activity and metabolites thereof. The present invention also relates to methods for synthesizing this type of anti-cancer medicines and methods for treating cancers using this type of compounds.

BACKGROUND OF THE INVENTION

Cancer is undoubtedly a refractory and life-threatening disease, and is also a common disease worldwide, thus it is a serious global health problem. In the United States, cancer is the leading cause of death among Americans under the age of 85; and is the second leading cause of death among older Americans. According to statistics, in the United States, about 1,500 people die of cancer every day, and there are about 3,400 new cases of cancer every day; while in China, about 1.8 million people die of cancer every year, and there are about 2.6 million new cases of cancer every year, and cancer has become the first leading cause of death among Chinese.

Cancer is a disease originating from body cells, and it is a malignant tumor. Such tumor cells are extremely abnormal and undergo random and disordered divisions, thus the growth and proliferation thereof are completely out of control. Cancer cells are very aggressive, and they attack and damage surrounding tissues. They can also leave the original tumor and enter the blood or lymphatic system, so as to form new tumors in other parts of the body.

Although there have been various anticancer medicines on the market, it is still an arduous task to treat cancer effectively, thus it remains an urgent priority to continue the research and development of anti-cancer medicines with higher activities and less toxic and side effects. Interestingly, compounds of halogenated nitro and nitroso estrogen can be used for treating cancers, especially breast cancer; more interestingly, it has also been found that aromatic halogenated nitro and nitroso compounds with simple structures have very high antitumor activities, especially for breast cancer (Kun et al. U.S. Pat. No. 5,464,871). Such compounds are inhibitors of poly(ADP-ribose) polymerase (PARP) which involves in DNA damage repair. Accordingly, DNA repair can be suppressed by inhibiting poly(ADP-ribose) polymerase, so as to enhance the therapeutic effects of radiotherapy and chemotherapy on cancers (Ossovskaya et al. US 20090149397; Sherman et al. US 20090131529 and 20090123419). In fact, the aromatic nitro compound is first converted into an aromatic nitroso compound in vivo, and the latter is the active compound that inhibits tumor growth. Due to the relatively poor water-solubility at physiological pH value and the limited stability, it is difficult to predict whether aromatic nitroso compounds can reach cancer cells, while aromatic nitro compounds do not have these problems, thus they are ideal prodrugs for aromatic nitroso compounds. Among such aromatic nitro compounds, 4-iodo-3-nitrobenzamide (INBA, Code BSI-201) is a very promising anti-cancer medicine. So far, this compound has entered into Phase III clinical trial and is further assessed for its anti-cancer effects in combination with other anticancer medicines, wherein the cancer treated is a metastatic triple-negative breast cancer (mTNBC).

Since organic iodide is very sensitive to light and air, and is poor in water-solubility, it is desirable to develop an iodine-free anti-cancer medicine having higher activity and better water-solubility. The present invention provides novel benzamide derivatives with anticancer activities, which are more effective iodine-free anticancer medicines than INBA (BSI-201).

SUMMARY OF THE INVENTION

One of the objectives of the present invention is to disclose a novel type of anticancer medicine—benzamide derivative or a pharmaceutically acceptable salt thereof.

The compound according to the present invention can be represented by formula (I):

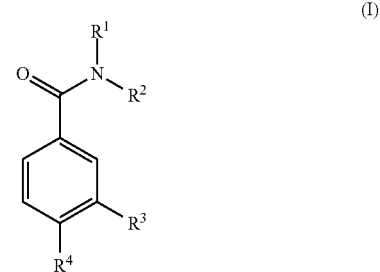

wherein $R^1$ and $R^2$ are independently selected from the group consisting of H, substituted or unsubstituted $(C_1-C_8)$alkyl, substituted or unsubstituted $(C_3-C_8)$alkenyl, substituted or unsubstituted $(C_3-C_8)$alkynyl, substituted or unsubstituted $(C_3-C_7)$cycloalkyl, —$COR^5$ and —$CO_2R^6$; $R^1$ and $R^2$ can also cyclize to form substituted or unsubstituted 4-, 5-, or 6-membered ring;

$R^3$ is nitro or nitroso;

$R^4$ is selected from the group consisting of ethynyl, propynyl or cyano;

$R^5$ is selected from the group consisting of substituted or unsubstituted $(C_1-C_8)$alkyl, substituted or unsubstituted $(C_3-C_8)$alkenyl, substituted or unsubstituted $(C_3-C_8)$alkynyl, substituted or unsubstituted $(C_3-C_7)$cycloalkyl, and substituted or unsubstituted aryl;

$R^6$ is selected from the group consisting of substituted or unsubstituted $(C_1-C_8)$alkyl, substituted or unsubstituted $(C_3-C_8)$alkenyl, substituted or unsubstituted $(C_3-C_8)$alkynyl, and substituted or unsubstituted $(C_3-C_7)$cycloalkyl;

Wherein, for the substituted or unsubstituted $(C_3-C_8)$alkenyl and the substituted or unsubstituted $(C_3-C_8)$alkynyl, it is preferable that the double bond of the alkenyl and the triple bond of the alkynyl are not directly connected to an amide nitrogen, a carbonyl or a carbonyloxy;

or a pharmaceutically acceptable salt thereof, or a prodrug thereof.

As used herein, if not particularly specified, the term "substituted" refers to being substituted by a radical selected from the group consisting of hydroxy, $(C_1-C_8)$alkyl, $(C_2-C_8)$alkenyl, $(C_2-C_8)$alkynyl, $(C_3-C_7)$cycloalkyl, $(C_1-C_8)$alkyloxy, amino, $(C_1-C_8)$alkylamino, di$(C_1-C_8)$alkylamino, —$(C_1-C_8)$alkylthio, and halogen, preferably hydroxy, methoxy, amino, methylamino, dimethylamino, methylthio, and halogen.

Wherein, $R^1$ and $R^2$ are preferably selected from the group consisting of hydrogen, substituted or unsubstituted $(C_1-C_8)$ alkyl, —COR⁵, or —CO₂R⁶; $R^1$ and $R^2$ can also cyclize to form a substituted or unsubstituted 4-, 5-, or 6-membered ring, wherein $R^5$ is a substituted or unsubstituted ($C_1$-$C_8$) alkyl, a substituted or unsubstituted ($C_3$-$C_8$)alkenyl, a substituted or unsubstituted ($C_3$-$C_8$)alkynyl, a substituted or unsubstituted ($C_3$-$C_7$)cycloalkyl, a substituted or unsubstituted aryl; $R^6$ is a substituted or unsubstituted ($C_1$-$C_8$)alkyl, a substituted or unsubstituted ($C_3$-$C_8$)alkenyl, a substituted or unsubstituted ($C_3$-$C_8$)alkynyl, a substituted or unsubstituted ($C_3$-$C_7$)cycloalkyl; wherein, for the substituted or unsubstituted ($C_3$-$C_8$)alkenyl and the substituted or unsubstituted ($C_3$-$C_8$)alkynyl, it is preferably that the double bond of the alkenyl and the triple bond of the alkynyl are not directly connected to an amide nitrogen, a carbonyl, or a carbonyloxy.

More preferably, $R^1$ and $R^2$ are independently selected from the group consisting of hydrogen, substituted or unsubstituted ($C_1$-$C_8$)alkyl, —COR⁵; or —CO₂R⁶; $R^1$ and $R^2$ can also cyclize to form a substituted or unsubstituted 4-, 5-, or 6-membered ring, wherein $R^5$ is a substituted or unsubstituted ($C_1$-$C_8$)alkyl, a substituted or unsubstituted ($C_3$-$C_7$)cycloalkyl, a substituted or unsubstituted aryl; $R^6$ is a substituted or unsubstituted ($C_1$-$C_8$)alkyl, a substituted or unsubstituted ($C_3$-$C_7$)cycloalkyl.

Most preferably, $R^1$ and $R^2$ are independently selected from the group consisting of hydrogen methyl, ethyl, propyl, —COR⁵, or —CO₂R⁶; $R^1$ and $R^2$ can also cyclize to form a substituted or unsubstituted 5- or 6-membered ring, and the ring formed may contain one or more heteroatoms, wherein the heteroatom is nitrogen, oxygen or sulfur atom, preferably nitrogen atom; $R^1$ and $R^2$ cyclize to form a substituted or unsubstituted 5- or 6-membered ring having one or more heteroatoms, preferably pyrrolidine ring, piperidine ring, morpholine ring, and piperazine ring.

Wherein, $R^5$ is preferably selected from substituted or unsubstituted ($C_1$-$C_8$)alkyl, and substituted or unsubstituted aryl, most preferably methyl, and phenyl.

Wherein, $R^6$ is preferably a substituted or unsubstituted ($C_1$-$C_8$)alkyl, more preferably methyl, ethyl, propyl, isopropyl, n-butyl or isobutyl, most preferably methyl, ethyl.

Wherein, $R^3$ is preferably selected from nitro or nitroso, more preferably nitro.

Wherein $R^4$ is preferably selected from the group consisting of ethynyl, propynyl, and cyano, more preferably ethynyl, and cyano.

More specifically, wherein the compound of formula (I) is selected from the group consisting of:
4-ethynyl-3-nitrobenzamide (I-1)
N-methoxycarbonyl-4-ethynyl-3-nitrobenzamide (I-2)
N-ethoxycarbonyl-4-ethynyl-3-nitrobenzamide (I-3)
N-propoxycarbonyl-4-ethynyl-3-nitrobenzamide (I-4)
N-butoxycarbonyl-4-ethynyl-3-nitrobenzamide (I-5)
N-isopropoxycarbonyl-4-ethynyl-3-nitrobenzamide (I-6)
N-isobutoxycarbonyl-4-ethynyl-3-nitrobenzamide (I-7)
4-cyano-3-nitrobenzamide (I-8)
N-methyl-4-ethynyl-3-nitrobenzamide (I-9)
N,N-dimethyl-4-ethynyl-3-nitrobenzamide (I-10)
N-acetyl-4-ethynyl-3-nitrobenzamide (I-11)
4-(1-propynyl)-3-nitrobenzamide (I-12)
N-benzoyl-4-ethynyl-3-nitrobenzamide (I-13)
N,N-diethyl-4-ethynyl-3-nitrobenzamide (I-14)
N,N-dipropyl-4-ethynyl-3-nitrobenzamide (I-15)
N,N-dibutyl-4-ethynyl-3-nitrobenzamide (I-16)
N-ethyl-4-ethynyl-3-nitrobenzamide (I-17)
N-propyl-4-ethynyl-3-nitrobenzamide (I-18)
N-butyl-4-ethynyl-3-nitrobenzamide (I-19)
(4-ethynyl-3-nitrophenyl)(pyrrolidin-1-yl)ketone (I-20)
(4-ethynyl-3-nitrophenyl)(piperidin-1-yl)ketone (I-21)
(4-ethynyl-3-nitrophenyl)(morpholin-4-yl)ketone (I-22)
(4-ethynyl-3-nitrophenyl)(piperazin-1-yl)ketone (I-23)
(4-ethynyl-3-nitrophenyl)(4-methylpiperazin-1-yl)ketone (I-24)
(4-ethynyl-3-nitrophenyl)(azetidinon-1-yl)ketone (I-25)
N-methyl-4-(1-propynyl)-3-nitrobenzamide (I-26)
N-methyl-4-cyano-3-nitrobenzamide (I-27)
4-ethynyl-3-nitrosobenzamide (I-28)
(4-ethynyl-3-nitrophenyl)(4-methylpiperazin-1-yl)ketone hydrochloride (I-29)
(4-ethynyl-3-nitrophenyl)(piperazin-1-yl)ketone hydrochloride (I-30).

The second aspect of the present invention also discloses the application of the compound of general formula (I) and the pharmaceutical composition thereof in the manufacture of a medicament for treating cancer. The cancer includes colon cancer, breast cancer, lung cancer, ovarian cancer, gastric cancer, acute leukemia, chronic leukemia, prostate cancer, human uterine cancer, pancreatic cancer, liver cancer, brain cancer, CNS tumor, bladder cancer, kidney cancer, skin cancer, neck cancer, myosarcoma, lymphoma, bone cancer and other types of cancers. Meanwhile, the present invention also discloses the application of the compound represented by general formula (I) and the pharmaceutical composition thereof in the manufacture of a medicament for treating conditions caused by, associated with, or accompanied with the destruction by cell proliferation and/or angiogenesis.

Another aspect of the present invention is to disclose the application of the compound of general formula (I) in the manufacture of a medicament for treating a disease associated with poly(ADP-ribose) polymerase (PARP) inhibitor. The disease associated with poly(ADP-ribose) polymerase (PARP) inhibitor includes cancer, stroke, myocardial infarction, neurodegenerative disease, etc. Another aspect of the present invention provides a method for treating diseases caused by, associated with or accompanied with the destruction by cell proliferation and/or angiogenesis, using effective amount of the compound represented by general formula (I) or the pharmaceutical composition containing the same alone or in combination with other medicines. The pharmaceutical composition according to the present invention can also comprise pharmaceutically acceptable carriers which are compatible with the compound of formula (I). The compound of formula (I) can be administered in common dosage forms, such as injectable and oral dosage forms, including capsule, tablet, powder, cachet, suspension or solution, preferably administered in an injectable manner. Dosage forms and pharmaceutical compositions can be prepared with commonly used pharmaceutically acceptable excipients and additives by common techniques. The pharmaceutically acceptable excipients and additives include non-toxic compatible fillers, binders, disintegrants, buffers, preservatives, antioxidants, lubricants, flavoring agents, thickeners, colorants, emulsifier, etc.

Another aspect of the present invention is to disclose a method for preparing the benzamide derivatives.

Another aspect of the present invention is to provide a method for preparing the compound of formula (I) (as shown in Equation 1). The method is applicable for the compound of formula (I) in which $R^1$ and $R^2$ are hydrogens, $R^3$ is nitro, $R^4$ is ethynyl, propynyl or cyano, such as for the preparation of Compound I-1, Compound I-8, and Compound I-12.

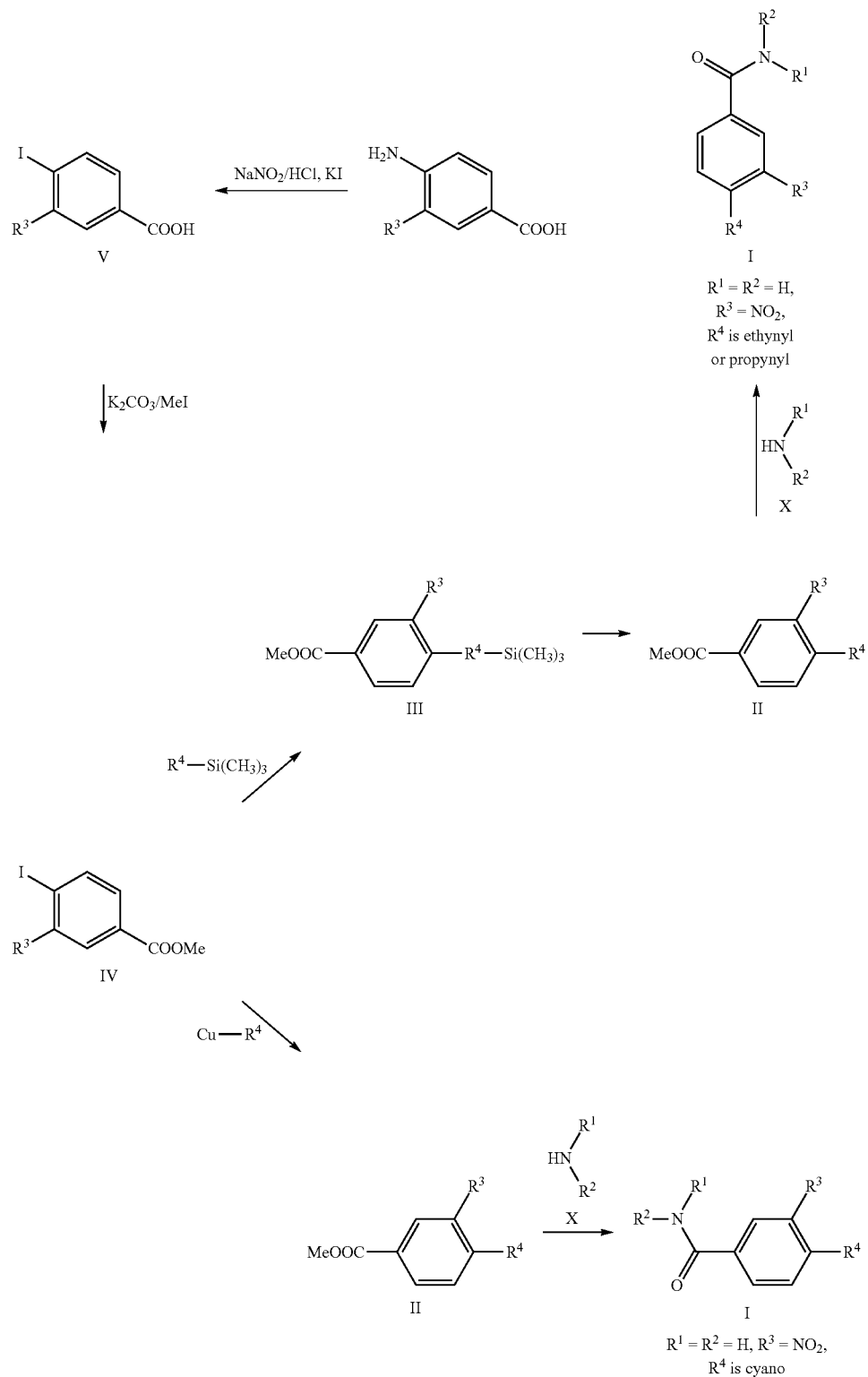

Equation 1

Another aspect of the present invention is to provide a method for preparing the compound of formula (I) using Compound IX as the starting material (as shown in Equation 2). The method is applicable for the compound of formula (I) in which $R^1$ is H, $R^2$ is —$COR^5$ or —$CO_2R^6$, $R^3$ is nitro, $R^4$ is ethynyl, propynyl or cyano, $R^5$ and $R^6$ are as defined above, such as for the preparation of Compound I-2, Compound I-3, Compound I-4, Compound I-5, Compound I-6, Compound I-7, Compound I-11 and Compound I-13.

Equation 2

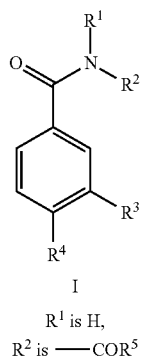

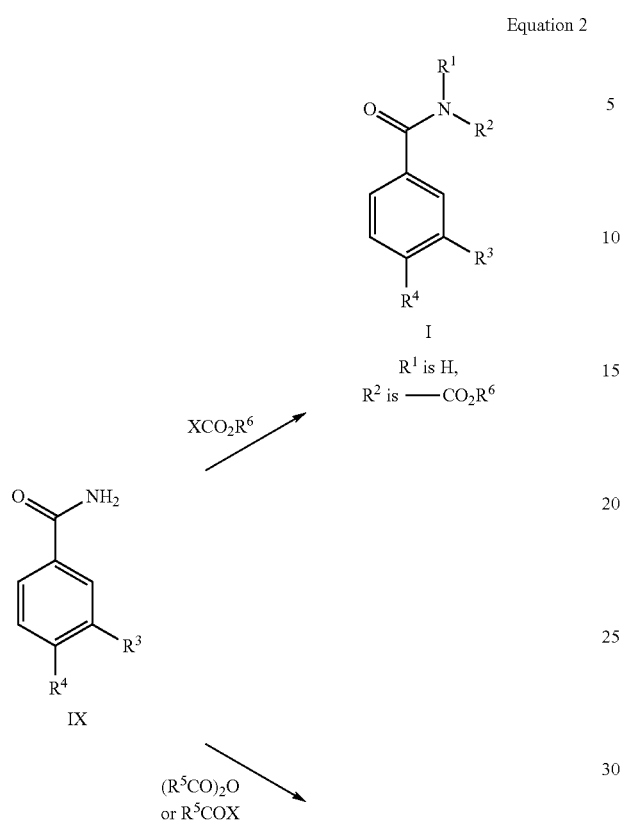

Another aspect of the present invention is to provide a method for preparing the compound of formula (I) (as shown in Equation 3). The method is applicable for the compound of formula (I) in which $R^1$ or $R^2$ is hydrogen, a substituted or unsubstituted $(C_1-C_8)$alkyl, a substituted or unsubstituted $(C_3-C_8)$alkenyl, a substituted or unsubstituted $(C_3-C_8)$alkynyl, a substituted or unsubstituted $(C_3-C_7)$cycloalkyl; $R^1$ and $R^2$ can also cyclize to form a substituted or unsubstituted 4-, 5-, or 6-membered ring, but $R^1$, $R^2$ can not be hydrogen at the same time; $R^3$ is nitro, $R^4$ is ethynyl, propynyl or cyano, such as for the preparation of Compound I-9, Compound I-10, Compound I-14, Compound I-15, Compound I-16, Compound I-17, Compound I-18, Compound I-19, Compound I-20, Compound I-21, Compound I-22, Compound I-23, Compound I-24, Compound I-25, Compound I-26, and Compound I-27.

Equation 3

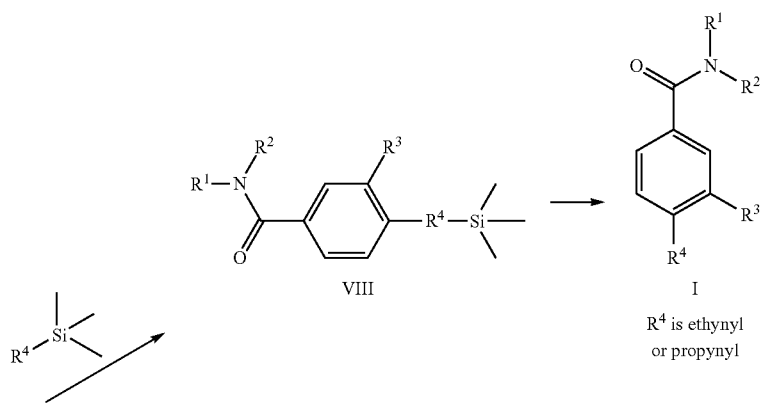

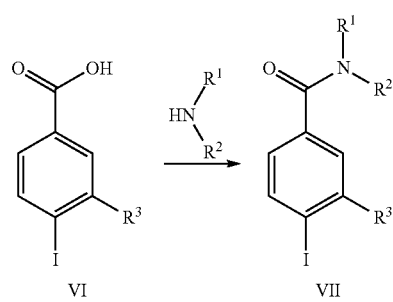

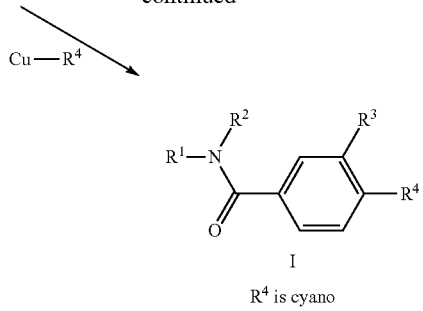

R⁴ is cyano

Another aspect of the present invention is to provide a method for preparing the compound of formula (I) (as shown in Equation 4). The method is applicable for the compound of formula (I) in which $R^1$ and $R^2$ are hydrogens, a substituted or unsubstituted $(C_1$-$C_8)$alkyl, a substituted or unsubstituted $(C_3$-$C_8)$alkenyl, a substituted or unsubstituted $(C_3$-$C_8)$alkynyl, a substituted or unsubstituted $(C_3$-$C_7)$cycloalkyl, —COR⁵, and —CO₂R⁶; $R^1$ and $R^2$ can also cyclize to form a substituted or unsubstituted 4-, 5-, or 6-membered ring; $R^3$ is nitroso; $R^4$ is ethynyl, propynyl or cyano; $R^5$ is a substituted or unsubstituted $(C_1$-$C_8)$alkyl, a substituted or unsubstituted $(C_3$-$C_8)$alkenyl, a substituted or unsubstituted $(C_3$-$C_8)$alkynyl, a substituted or unsubstituted $(C_3$-$C_7)$cycloalkyl, a substituted or unsubstituted aryl; $R^6$ is a substituted or unsubstituted $(C_1$-$C_8)$alkyl, a substituted or unsubstituted $(C_3$-$C_8)$alkenyl, a substituted or unsubstituted $(C_3$-$C_8)$alkynyl, a substituted or unsubstituted $(C_3$-$C_7)$cycloalkyl, such as for the preparation of Compound I-28.

Equation 4

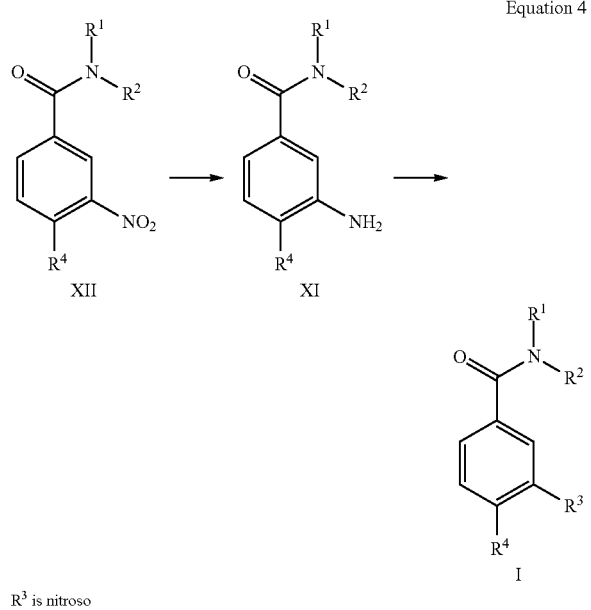

R³ is nitroso

The present invention also provide a method for the compound of formula (I) to form a salt with an acid: mixing the compound of formula (I) of the present invention adequately with a corresponding acid (such as hydrochloric acid, sulfuric acid, etc.), to obtain the corresponding salt through aftertreatment, such as for the preparation of Compound I-29 and I-30.

Some of the terms used herein are defined as follows:

"Halogen" refers to fluorine, chlorine, bromine and iodine, preferably chlorine, bromine and iodine.

"Alkyl", as a group or part of a group, refers to a straight or branched aliphatic hydrocarbon group. $(C_1$-$C_8)$alkyl is preferred. The example of alkyl group includes, but not limited to, methyl, ethyl, n-propyl, 2-propyl, n-butyl, isobutyl, tert-butyl, hexyl, etc.

"Alkenyl", as a group or part of a group, refers to an aliphatic hydrocarbon group with a carbon-carbon double bond, which can be straight or branched. $(C_3$-$C_8)$alkenyl is preferred. The example of alkenyl group includes, but not limited to, allyl, 2-butenyl, etc.

"Alkynyl", as a group or part of a group, refers to an aliphatic hydrocarbon group with a carbon-carbon triple bond, which can be straight or branched. $(C_3$-$C_8)$alkynyl is preferred. The example of alkynyl group includes, but not limited to, propargyl, 2-butynyl, etc.

"Heterocyclic group" refers to an aromatic or non-aromatic heterocyclic group in which one or more ring atoms are heteroatoms, such as oxygen, nitrogen, sulfur, etc. Aromatic heterocyclic group, i.e. commonly referred "heteroaryl", preferably refers to an aromatic 5 to 6-membered monocyclic ring or 9 to 10-membered bicyclic ring, which can comprise 1, 2, or 3 atoms selected from the group consisting of nitrogen, oxygen and/or sulfur, for example, furyl, pyridyl, 2-oxo-1,2-dihydropyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzimidazolyl, indolyl, isoindolyl, 1,3-dioxo-isoindolyl, quinolyl, indazole, benzoisothiazolyl, benzoxazolyl, and benzoisoxazolyl. A preferred heteroaryl is pyridyl. Heteroaryl can have the substituents as described for the above term "aryl". Non-aromatic heterocyclic group refers to a non-aromatic heterocyclic group preferably having 5- to 6-membered monocyclic ring or 8- to 10-membered bicyclic or tricyclic ring, which can comprise 1, 2, or 3 atoms selected from the group consisting of nitrogen, oxygen and/or sulfur, for example, morpholinyl, thiomorpholinyl, tetrahydropyranyl, 1,1-dioxo-thiomorpholinyl, piperidyl, 2-oxo-piperidinyl, pyrrolidinyl, 2-oxo-pyrrolidinyl, piperazin-2-one, 8-oxa-3-aza-bicyclo[3.2.1]octyl, and piperazinyl. Heterocyclic group can optionally have the substituents as described for the above term "aryl".

In addition, the term "pharmaceutically acceptable salt" refers to certain salts of the above compounds, which can maintain the original bioactivities and are suitable for medical use. The pharmaceutically acceptable salt of the compound represented by formula (I) can be a metal salt, an amine salt formed with suitable acid, wherein the metal salt is preferably selected from alkaline metal salt, alkaline earth metal salt, and the suitable acid includes inorganic acid and organic acid, such as acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, malic acid, maleic acid, mandelic acid, methanesulfonic acid, nitric acid, phosphoric acid, succinic acid, sulfuric acid, tartaric acid, p-toluenesulfonic acid, etc. Hydrochloric acid, hydrobromic acid, phosphoric acid, and sulfuric acid are especially preferred, and hydrochloride is most preferred.

"Cycloalkyl" refers to saturated or partially saturated monocyclic, fused or spiro carbon ring. A ring formed with 3 to 7 carbons is preferred. The example includes, but not limited to, cyclopropyl, cyclobutyl, cyclopentyl, cyclohexyl, etc.

"Alkoxy" refers to "alkyl-O—" group. Wherein, alkyl is as defined in the corresponding definition herein. $(C_1-C_6)$alkoxy is preferred. Examples thereof include, but not limited to, methoxy, ethoxy, n-propoxy, isopropoxy, n-butoxy, isobutoxy, tert-butoxy, etc.

The term "aryl", used alone or in combination, refers to a carbocyclic aromatic system having one or two rings, wherein the rings can be connected together in a fused manner. The term "aryl" includes aromatic groups such as phenyl, naphthyl, and tetrahydronaphthyl. The preferred aryl is $(C_6-C_{10})$aryl, more preferred aryl is phenyl. The "aryl" may have one or more substituents, such as $(C_1-C_6)$alkyl, hydroxy, halogen, halogenoalkyl, nitro, cyano, $(C_1-C_6)$alkoxy, $(C_1-C_6)$ alkylamino, etc.

We have already found that the compounds according to the present invention are highly active inhibitors of tumor growth.

The present invention is further illustrated by the following examples. The examples provide the preparation of representative compounds of formula (I) and related data for structural identification. It must be noted that the following examples are intended to illustrate the present invention rather than to limit the present invention.

In the following examples, unless otherwise specified, all the temperatures are Celsius temperatures, and unless otherwise specified, various starting material and reagent are obtained commercially. Commercially available starting materials and reagents are used directly without further purification, unless otherwise specified.

The glassware are dried by oven and/or heating. The reactions are monitored on glass Silica gel-60 F254 plates (0.25 mm) (TLC). Analytical thin-layer chromatography is carried out to develop in an appropriate solvent ratio (v/v). The reaction is completed when the starting materials on TLC are depleted.

$^1$H NMR spectra are measured and obtained by using a Bruker instrument (400 MHz), with chemical shifts represented by ppm. Tetramethylsilane is used as the internal standard (0.00 ppm). $^1$H NMR representation: s=single, d=doublet, t=triplet, m=multiplet, br=broadened, dd=doublet of doublet, dt=doublet of triplet. Coupling constant is in Hz, if provided.

Mass spectra are measured and obtained by using LC/MS instrument, and the ionization mode can be ESI or APCI.

All the melting points are not corrected.

The following examples are only intended to illustrate the synthetic method of specific compounds of the present invention. But the synthetic method is not limited in any way. Compounds which are not listed below can also be prepared using the same synthetic routes and synthetic methods below, by selecting appropriate starting materials, and slightly and appropriately adjusting, if necessary, the reaction conditions according to commonsense.

DETAILED EMBODIMENTS

Example 1

Preparation of 4-iodo-3-nitrobenzoic acid (Compound V)

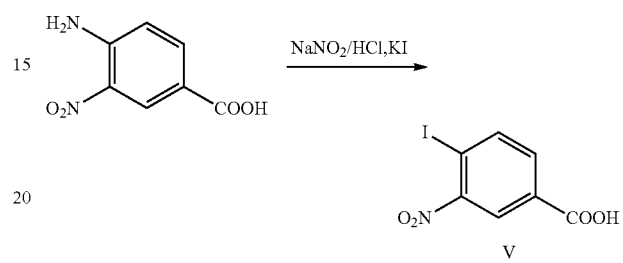

45 g (0.25 mol) 4-Amino-3-nitrobenzoic acid, 400 ml water and 100 ml concentrated hydrochloric acid were added into a reaction flask. Started to stir, and the mixture was cooled to 0 to 5° C., then 50 ml aqueous solution of 25.9 g sodium nitrite (0.38 mol) was added dropwise. The solid was dissolved gradually. After completing the dropwise addition, the mixture was reacted at 0 to 5° C. for 1 hour, and 200 ml aqueous solution of 88 g (0.5 mol) potassium iodide was added dropwise at this temperature. The mixture was stirred at room temperature for 2 h after completing the dropwise addition, and solid was precipitated. The solid was filtered, washed with water, and dried to obtain 4-iodo-3-nitrobenzoic acid (compound V) as a solid, 65 g (0.22 mol), yield 89.7%.

Example 2

Preparation of methyl 4-iodo-3-nitrobenzoate (Compound IV)

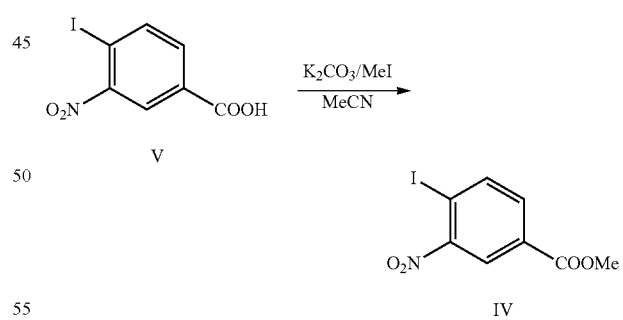

55 g (0.19 mol) 4-Iodo-3-nitrobenzoic acid (Compound V), 16.5 g (0.12 mol) potassium carbonate and 550 ml acetonitrile were added into a reaction flask, and started to stir. The mixture was cooled to 0 to 5° C., and 52.9 ml (0.38 mol) triethylamine was added. The temperature was controlled below 10° C., and 71 ml (1.12 mol) iodomethane was added. The mixture was heated to about 40° C. for 8 hours, and concentrated under reduced pressure after completing the reaction until most of the acetonitrile was evaporated. The mixture was then extracted with 500 ml ethyl acetate, washed with water for three times, and the organic layer was dried over anhydrous sodium sulfate, filtered, and the filtrate was concentrated to the least amount, and then 300 ml petroleum ether was added, stirred for 30 min, and then filtered. The filter cake was washed with petroleum ether, and dried to obtain methyl 4-iodo-3-nitrobenzoate (Compound IV), about 41.2 g (0.13 mol), yield 71.5%.

¹HNMR (400 MHz, DMSO-d₆): δ 3.91 (s, 3H), 7.87 (dd, 1H, J₁=8.08 Hz, J₂=1.88 Hz), 8.26 (d, 1H, J=8.12 Hz), 8.34 (d, 1H, J=9.12 Hz); MS (m/z): 308 [M+H].

Example 3

Preparation of methyl 4-(2-trimethylsilyl)ethynyl-3-nitrobenzoate (compound III)

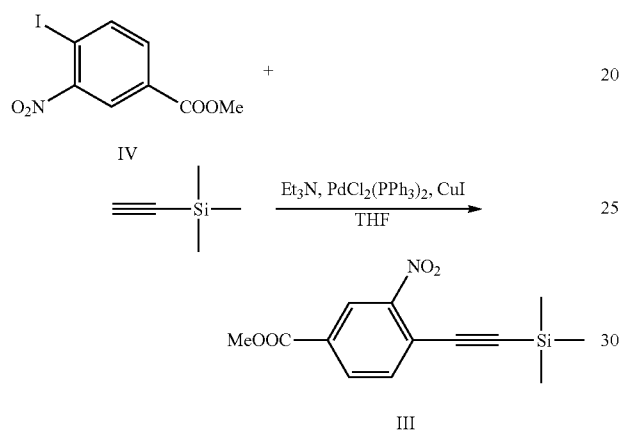

25 g (0.08 mol) Methyl 4-iodo-3-nitrobenzoate (compound IV), 20 ml (0.14 mol) triethylamine and 200 ml tetrahydrofuran were added into a reaction flask, protected by nitrogen gas, and stirred to dissolve, then 2.4 g (0.0034 mol) bis(triphenylphosphine)palladium dichloride, 0.65 g (0.0034 mol) cuprous iodide and 13.7 ml (0.096 mol) trimethylsilylethyne were added, the mixture was reacted at room temperature for 1 hour, concentrated under reduced pressure to evaporated most of the tetrahydrofuran. After extracting with 300 ml ethyl acetate, the organic layer was washed with water for three times, dried over anhydrous sodium sulfate, filtered, and the filtrate was concentrated to dryness and separated by column chromatography to obtain methyl 4-(2-(trimethylsilyl)ethynyl-3-nitrobenzoate (Compound III), 15.1 g (0.055 mol), yield 66.9%.

¹HNMR (400 MHz, DMSO-d₆): δ 0.09 (s, 9H), 3.74 (s, 3H), 7.69 (d, 1H, J=8.08 Hz), 8.00 (dd, 1H, J₁=8.08 Hz, J₂=1.52 Hz), 8.30 (d, 1H, J=1.36 Hz); MS (m/z): 278 [M+H].

Example 4

Preparation of methyl 4-ethynyl-3-nitrobenzoate (Compound II-1)

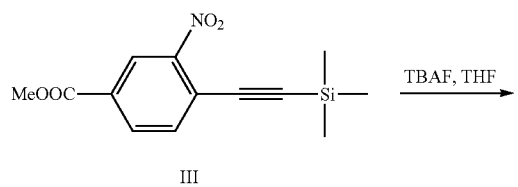

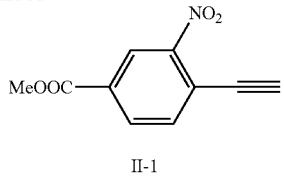

15 g (0.054 mol) Methyl 4-(2-trimethylsilyl)ethynyl-3-nitrobenzoate (Compound III) and 225 ml tetrahydrofuran were added into a reaction flask, and started to stir, and cooled to −20 to −25° C., then 35 ml solution of 7.1 g (0.027 mol) tetrabutylammonium fluoride in tetrahydrofuran was added dropwise, and continued to react for 20 min after completing the dropwise addition. After the completion of the reaction monitored by TLC, the pH was adjusted to 4~5 by adding 0.5 M hydrochloric acid. The mixture was concentrated under reduced pressure to evaporated most of the tetrahydrofuran, and then extracted with 300 ml ethyl acetate, the organic layer was washed with water for three times, dried over anhydrous sodium sulfate, filtered, and the filtrate was concentrated to dryness, to obtain about 10.5 g crude product, which was separated by column chromatography to obtain methyl 4-ethynyl-3-nitrobenzoate (compound II-1), 7.3 g (0.036 mol), yield 65.8%.

¹HNMR (400 MHz, DMSO-d₆): δ 3.93 (s, 3H), 5.02 (s, 1H), 7.93 (d, 1H, J=8.08 Hz), 8.21 (dd, 1H, J₁=8.08 Hz, J₂=1.64 Hz), 8.50 (d, 1H, J=1.48 Hz); MS (m/z): 206 [M+H].

Example 5

Preparation of 4-ethynyl-3-nitrobenzamide (Compound I-1)

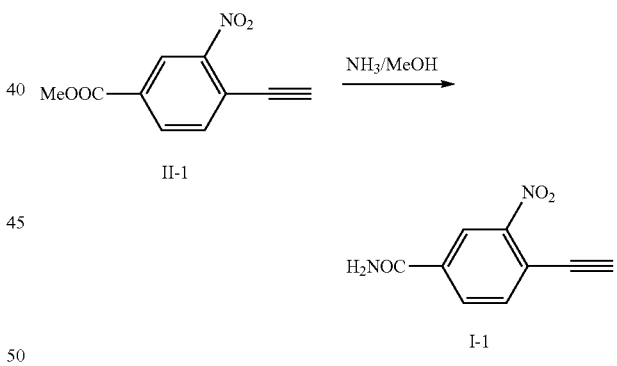

7.3 g (0.036 mol) Methyl 4-ethynyl-3-nitrobenzoate (Compound II-1), 300 ml methanol and 200 ml tetrahydrofuran were added into a reaction flask, stirred, and ammonia gas was passed through for 1 hour. Then the mixture was reacted at room temperature for 24 hours. After completion of the reaction monitored by TLC, the mixture was concentrated under reduced pressure with most of the tetrahydrofuran and methanol evaporated, then extracted with 300 ml ethyl acetate. The organic layer was washed with water for three times, dried over anhydrous sodium sulfate, filtered, and the filtrate was concentrated to dryness, and separated by column chromatography to obtain 4-ethynyl-3-nitrobenzamide (compound I-1), 3.6 g (0.0019 mol), yield 53.2%.

¹HNMR (400 MHz, DMSO-d₆): 4.93 (s, 1H), 7.82 (s, 1H), 7.92 (d, 1H, J=8.08 Hz), 8.21 (dd, 1H, J₁=8.04 Hz, J₂=1.68 Hz), 8.37 (s, 1H), 8.57 (d, 1H, J=1.56 Hz); MS (m/z): 191 [M+H].

Example 6

Preparation of N-methoxycarbonyl-4-ethynyl-3-nitrobenzamide (Compound I-2)

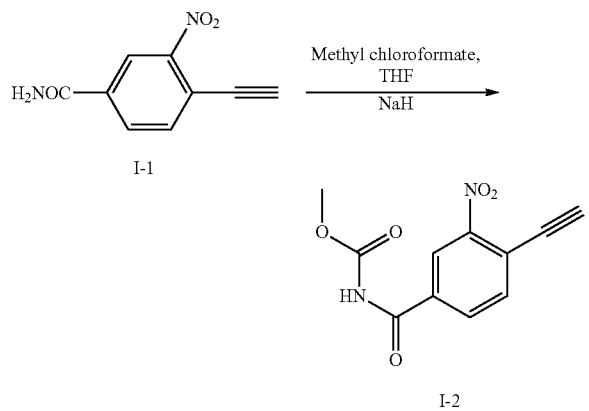

3 g (0.016 mol) 4-Ethynyl-3-nitrobenzamide (Compound I-1), 45 ml tetrahydrofuran and 6 ml methyl chloroformate were added into a 100 ml four-neck reactor flask, stirred to dissolve and cooled to −10° C., and 7.5 g sodium hydride was added and maintained at about 0° C. for 30 minutes. After the completion of the reaction, the reaction mixture was poured into crushed ice and the pH was adjusted to acidic with hydrochloric acid, and then extracted with 200 ml ethyl acetate. The organic layer was washed with water for three times, and dried over anhydrous sodium sulfate, filtered, and the filtrate was concentrated to dryness to obtain about 3.5 g crude product, which was separated by column chromatography to obtain N-methoxycarbonyl-4-ethynyl-3-nitrobenzoateamide (Compound I-2), 1.6 g (0.0065 mol), yield 40.8%.

$^1$HNMR (400 MHz, DMSO-$d_6$): δ 3.76 (s, 3H), 4.98 (s, 1H), 7.91 (d, 1H, J=8.08 Hz), 8.18 (dd, 1H, $J_1$=8.08 Hz, $J_2$=1.80 Hz), 8.58 (d, 1H, J=1.72 Hz), 11.36 (s, 1H); MS (m/z): 249 [M+H].

The following compounds were prepared according to the method of Example 6 by selecting appropriate reagents, using Compound I-1 as starting material.

| Example | Name | Structure | $^1$H NMR and MS (m/z) |
|---|---|---|---|
| 7 | N-ethoxy-carbonyl-4-ethynyl-3-nitrobenzamide | I-3 | $^1$HNMR (400 MHz, DMSO-$d_6$): δ 1.29 (t, 3H), 4.21 (m, 2H), 4.98 (s, 1H), 7.92 (d, 1H, J = 8.08 Hz), 8.18 (dd, 1H, $J_1$ = 8.08 Hz, $J_2$ = 1.72 Hz), 8.58 (d, 1H, J = 1.68 Hz), 11.33 (s, 1H); MS (m/z): 261 [M − H] |
| 8 | N-propoxy-carbonyl-4-ethynyl-3-nitrobenzamide | I-4 | $^1$HNMR (400 MHz, DMSO-$d_6$): δ 0.94 (t, 3H), 1.65 (m, 2H), 4.11 (t, 2H), 7.92 (d, 1H, J = 8.1 Hz), 8.17 (dd, 1H, $J_1$ = 8.1 Hz, $J_2$ = 1.8 Hz), 8.56 (d, 1H, J = 1.7 Hz), 11.31 (s, 1H); MS (m/z): 275 [M − H] |
| 9 | N-butoxy-carbonyl-4-ethynyl-3-nitrobenzamide | I-5 | $^1$HNMR (400 MHz, DMSO-$d_6$): δ 0.92 (t, 3H), 1.38 (m, 2H), 1.64 (m, 2H), 4.15 (t, 2H), 4.98 (s, 1H), 7.92 (d, 1H, J = 8.08 Hz), 8.17 (dd, 1H, $J_1$ = 8.12 Hz, $J_2$ = 1.76 Hz), 8.57 (d, 1H, J = 1.72 Hz), 11.30 (s, 1H); MS (m/z): 313 [M + Na] |

| Example | Name | Structure | $^1$H NMR and MS (m/z) |
|---|---|---|---|
| 10 | N-isopropoxycarbonyl-4-ethynyl-3-nitrobenzamide | I-6 | $^1$HNMR (400 MHz, DMSO-$d_6$): δ 1.30 (d, 6H, J = 6.24 Hz), 4.97 (m, 2H), 7.92 (d, 1H, J = 8.08 Hz), 8.19 (dd, 1H, $J_1$ = 8.04 Hz, $J_2$ = 1.00 Hz), 8.59 (s, 1H), 11.26 (s, 1H); MS (m/z): 275 [M − H] |
| 11 | N-isobutoxycarbonyl-4-ethynyl-3-nitrobenzamide | I-7 | $^1$HNMR (400 MHz, DMSO-$d_6$): δ 0.95 (d, 6H, J = 6.68 Hz), 1.95 (m, 1H), 3.94 (d, 2H, J = 6.64 Hz), 4.97 (s, 1H), 7.92 (d, 1H, J = 8.08 Hz), 8.17 (dd, 1H, $J_1$ = 8.08 Hz, $J_2$ = 1.72 Hz), 8.57 (d, 1H, J = 1.64 Hz), 11.28 (s, 1H); MS (m/z): 313 [M + Na] |

Example 12

Preparation of methyl 4-cyano-3-nitrobenzoate (Compound II-8)

Example 13

Preparation of 4-cyano-3-nitrobenzamide (Compound I-8)

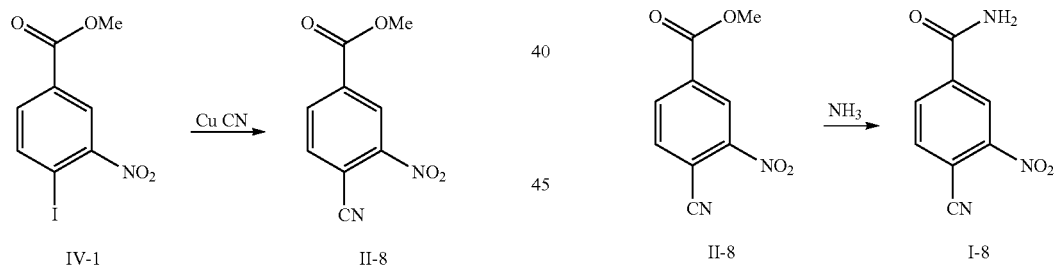

5 g (0.016 mol) Methyl 4-iodo-3-nitrobenzoate (Compound IV-1), 1.77 g (0.02 mol) cuprous cyanide and 15 ml hexamethylphosphoric triamide were added into a reaction flask, and heated to 100° C. and reacted for 1 hour. After the reaction was completed, the mixture was cooled to room temperature, then extracted with 100 ml ethyl acetate, and the organic layer was washed with water for three times, dried over anhydrous sodium sulfate, filtered, and the filtrate was concentrated to dryness, separated by column chromatography to obtain methyl 4-cyano-3-nitrobenzoate (Compound II-8), 2.7 g (0.013 mol), yield 80.4%.

$^1$HNMR (400 MHz, DMSO-$d_6$): δ 3.96 (s, 3H), 8.34 (d, 1H, J=7.9 Hz), 8.42 (d, 1H, J=7.7 Hz), 8.68 (s, 1H); MS (m/z): 229 [M+Na].

2 g (9.71 mmol) Methyl 4-cyano-3-nitrobenzoate (Compound II-8) and 60 ml methanol were added into a reaction flask, stirred, and ammonia gas was passed through for 1 hour, then reacted for 8 hours at room temperature. After the reaction was completed, the mixture was concentrated under reduced pressure to evaporate most of the methanol. Then the mixture was extracted with 100 ml ethyl acetate, and the organic layer was washed with water for three times, dried over anhydrous sodium sulfate, filtered, and the filtrate was concentrated to dryness to obtain 1.1 g (5.76 mmol) crude product, which was recrystallized from ethyl acetate-n-hexane to obtain 4-cyano-3-nitrobenzamide (compound I-8), 0.6 g, yield 32.6%.

$^1$HNMR (400 MHz, DMSO-$d_6$): δ 7.97 (s, 1H), 8.32 (d, 1H, J=7.96 Hz), 8.39 (dd, 1H, $J_1$=7.96 Hz, $J_2$=1.56 Hz), 8.53 (s, 1H), 8.78 (d, 1H, J=1.52 Hz); MS (m/z): 190 [M−H].

Example 14

Preparation of N-methyl-4-iodo-3-nitrobenzamide (Compound VII-1)

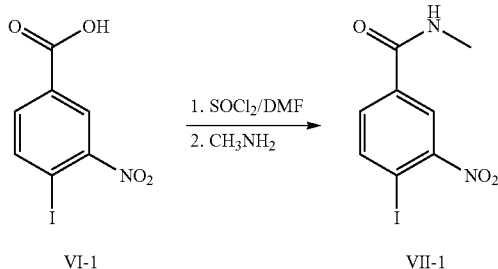

10 g (0.034 mol) 4-Iodo-3-nitrobenzoic acid (Compound VI-1) and 50 ml N,N-dimethylformamide were added into a reaction flask, stirred to dissolve, and cooled to below 10° C., and 7.5 ml (0.10 mol) sulfoxide chloride was added. After completion of the dropwise addition, the mixture was warmed to room temperature and reacted for one hour. The reaction mixture was poured into 200 ml aqueous solution of 30% methylamine with low temperature, stirred for 5 minutes to precipitate a solid, and then the mixture was added with 500 ml ice-water, stirred for 10 minutes, filtered. The solid was washed with water and dried to obtain N-methyl-4-iodo-3-nitrobenzamide (Compound VII-1), 6.5 g (0.021 mol), yield 62.3%.

$^1$HNMR (400 MHz, DMSO-$d_6$): δ 2.81 (d, 3H, J=4.1 Hz), 7.84 (d, 1H, 7.8 Hz), 8.23 (d, 1H, J=8.1 Hz), 8.33 (s, 1H), 8.75 (s, 1H); MS (m/z): 307 [M+H].

Example 15

Preparation of N-methyl-4-(2-trimethylsilyl)ethynyl-3-nitrobenzamide (Compound VIII-1)

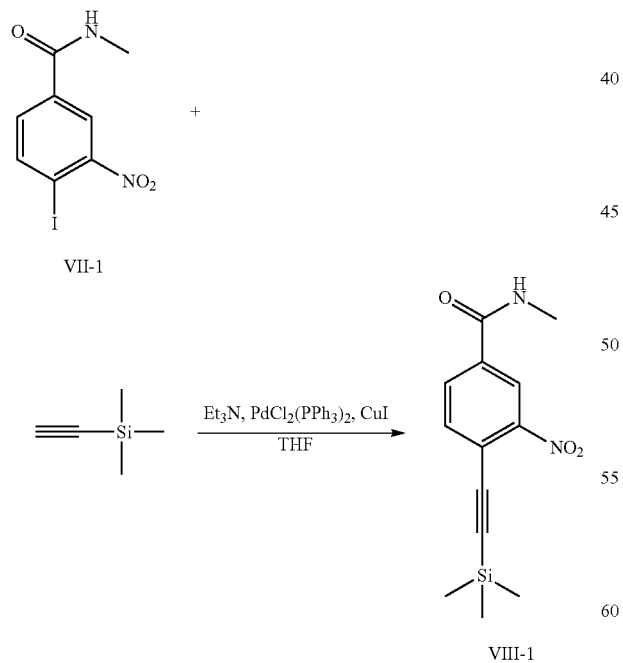

6 g (0.02 mol) N-Methyl-4-iodo-3-nitrobenzamide (Compound VII-1), 60 ml tetrahydrofuran and 4.2 ml triethylamine, were added into a 100 ml four-neck flask, stirred to dissolve, and 0.44 g (0.63 mmol) bis(triphenylphosphine) palladium dichloride, 0.24 g (1.26 mmol) cuprous iodide and 6 ml (0.042 mol) trimethylsilylacetylene were added, and reacted at room temperature for 1 h. Most of tetrahydrofuran was evaporated by concentration under reduced pressure, and the mixture was extracted by adding 200 ml ethyl acetate, then the organic layer was washed with water for three times, dried over anhydrous sodium sulfate, filtered, and the filtrate was concentrated to dryness, separated by column chromatography to obtain 3.8 g (0.014 mol) N-methyl-4-(2-trimethylsilyl)ethynyl-3-nitrobenzamide (Compound VIII-1) as a solid, yield 70.2%.

$^1$HNMR (400 MHz, DMSO-$d_6$): δ 0.26 (s, 9H), 2.81 (d, 3H, J=4.5 Hz), 7.87 (d, 1H, J=8.1 Hz), 8.14 (dd, 1H, $J_1$=8.1 Hz, $J_2$=1.6 Hz), 8.52 (d, 1H, J=1.5 Hz), 8.83 (d, 1H, J=4.4 Hz); MS (m/z): 277 [M+H].

Example 16

Preparation of N-methyl-4-ethynyl-3-nitrobenzamide (Compound I-9)

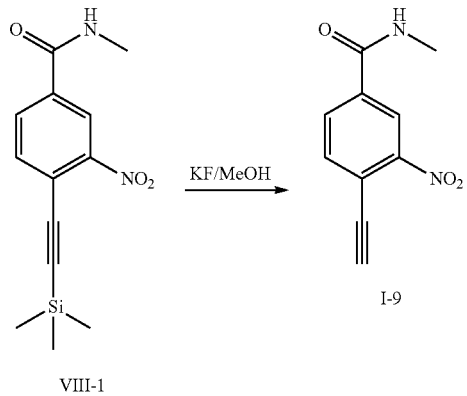

3.3 g (0.012 mol) N-Methyl-4-(2-trimethylsilyl)ethynyl-3-nitrobenzamide (Compound VIII-1) and 20 ml methanol were added into a 100 ml reaction flask, stirred to dissolve, and 0.53 g (0.0056 mol) potassium fluoride dihydrate was added and reacted for 30 minutes. After the reaction was completed, the mixture was dropwise added with 60 ml water, filtered and dried to obtain 2.2 g solid, which was recrystallized from ethyl acetate-n-hexane, to obtain N-methyl-4-ethynyl-3-nitrobenzamide (Compound I-9), 1.5 g (0.0074 mol), yield 61.7%.

$^1$HNMR (400 MHz, DMSO-$d_6$): δ 2.82 (d, 3H, J=4.56 Hz), 4.92 (s, 1H), 7.92 (d, 1H, J=8.08 Hz), 8.17 (dd, 1H, $J_1$=8.08 Hz, $J_2$=1.76 Hz), 8.54 (d, 1H, J=1.64 Hz), 8.86 (d, 1H, J=4.32 Hz); MS (m/z): 203 [M−H].

Example 17

Preparation of N,N-dimethyl-4-ethynyl-3-nitrobenzamide (Compound I-10)

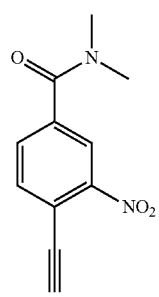

Compound I-10 was prepared according to the methods of Example 14, Example 15 and Example 16, using the compound 4-iodo-3-nitrobenzoic acid (Compound VI-1) and dimethylamine as starting materials:

¹HNMR (400 MHz, CDCl₃): δ 3.02 (s, 3H), 3.14 (s, 3H), 3.62 (s, 1H), 7.67 (dd, 1H, J₁=7.96 Hz, J₂=1.64 Hz), 7.74 (d, 1H, J=7.92 Hz), 8.12 (d, 1H, J=1.56 Hz); MS (m/z): 219 [M+H]

Example 18

Preparation of N-acetyl-4-ethynyl-3-nitrobenzamide (Compound I-11)

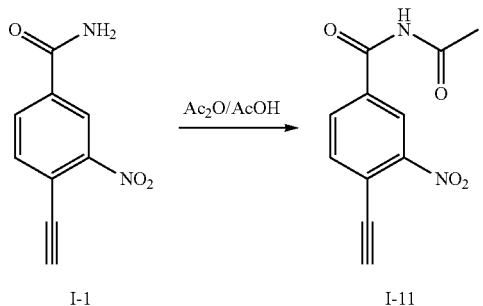

I-1   I-11

4 g (0.021 mol) 4-Ethynyl-3-nitrobenzamide (Compound I-1), 30 ml (0.320 mol) acetic anhydride and 20 ml acetic acid were added into a reaction flask, stirred, and heated to 120° C. for 15 hours. After completion of the reaction monitored by TLC, the mixture was extracted with 300 ml ethyl acetate, and the organic layer was washed with water for three times, dried over anhydrous sodium sulfate, filtered, and the filtrate was concentrated to dryness, separated by column chromatography to obtain N-acetyl-4-ethynyl-3-nitrobenzamide (Compound I-11), 1.1 g (0.0047 mol), yield 22.6%.

¹HNMR (400 MHz, DMSO-d₆): δ 2.36 (s, 3H), 4.99 (s, 1H), 7.94 (d, 1H, J=8.08 Hz), 8.21 (dd, 1H, J₁=8.12 Hz, J₂=1.80 Hz), 8.60 (d, 1H, J=1.72 Hz), 11.32 (s, 1H); MS (m/z): 231 [M−H].

Example 19

Preparation of 4-(1-propynyl)-3-nitrobenzamide (Compound I-12)

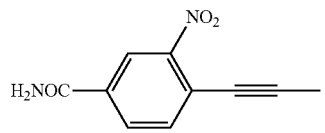

I-12

Compound I-12 was prepared according to the methods of Example 3, Example 4 and Example 5, using the compound methyl 4-iodo-3-nitrobenzoate (Compound IV) and trimethylpropargylsilane as starting materials:

¹HNMR (400 MHz, DMSO-d₆): δ 2.16 (s, 3H), 7.74 (s, 1H), 7.79 (d, 1H, J=8.16 Hz), 8.14 (dd, 1H, J₁=8.13 Hz, J₂=1.77 Hz), 8.30 (s, 1H), 8.50 (d, 1H, J=1.71 Hz); MS (m/z): 203 [M−H].

Example 20

Preparation of N-benzoyl-4-ethynyl-3-nitrobenzamide (Compound I-13)

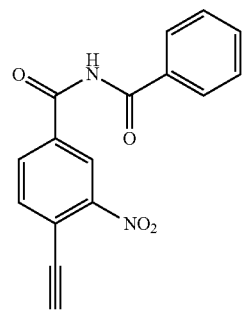

I-13

Compound I-13 was prepared according to the method of Example 6, using Compound I-1 and benzoyl chloride as starting materials:

¹HNMR (400 MHz, DMSO-d₆): δ 4.89 (s, 1H), 7.54 (t, 2H, J=7.5 Hz), 7.66 (t, 1H, J=7.4 Hz), 7.91-7.96 (m, 3H), 8.20 (dd, 1H, J=8.1 Hz, J₂=1.6 Hz), 8.58 (d, 1H, J=1.5 Hz), 11.52 (s, 1H); MS (m/z): 293 [M−H].

Compound I-14, Compound I-15, Compound I-16, Compound I-17, Compound I-18, Compound I-19, Compound I-20, Compound I-21, Compound I-22, Compound I-23, Compound I-24 and Compound I-25 were prepared sequentially according to the methods of Example 14, Example 15 and Example 16, by selecting appropriate amines and trimethylsilylacetylene, using the Compound 4-iodo-3-nitrobenzoic acid (Compound VI-1) as starting material; Compound I-26 was prepared sequentially according to the methods of Example 15 and Example 16, using the compound N-methyl-4-iodo-3-nitrobenzamide (Compound VII-1) and trimethylpropargylsilane as starting materials:

| Example | Name | Structure | ¹H NMR and MS (m/z) |
|---|---|---|---|
| 21 | N,N-diethyl-4-ethynyl-3-nitrobenzamide | 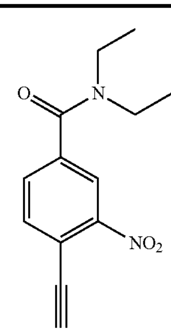 | ¹HNMR (400 MHz, DMSO-d₆): δ 1.08 (br s, 3H), 1.18 (br s, 3H), 3.21 (m, 2H), 3.46 (m, 2H), 4.83 (s, 1H), 7.76 (dd, 1H, J₁ = 7.9 Hz, J₂ = 1.6 Hz), 7.85 (d, 1H, J = 7.9 Hz), 8.09 (d, 1H, J = 1.4 Hz); MS (m/z): 247 [M + H] |

I-14

-continued

| Example | Name | Structure | ¹H NMR and MS (m/z) |
|---|---|---|---|
| 22 | N,N-dipropyl-4-ethynyl-3-nitro-benzamide | I-15 | ¹HNMR (400 MHz, DMSO-d$_6$): δ 0.70 (t, 3H, J = 6.7 Hz), 1.51 (m, 2H), 1.63 (m, 2H), 3.13 (t, 2H), 3.38 (t, 2H, J = 6.6 Hz), 4.83 (s, 1H), 7.74 (dd, 1H, J$_1$ = 7.9 Hz, J$_2$ = 1.4 Hz), 7.85 (d, 1H, J = 7.9 Hz), 8.07 (d, 1H, J = 1.3 Hz); MS(m/z): 275 [M + H] |
| 23 | N,N-dibutyl-4-ethynyl-3-nitro-benzamide | I-16 | ¹HNMR (400 MHz, DMSO-d$_6$): δ 0.73 (t, 3H, J = 7.0 Hz), 0.94 (t, 3H, J = 7.1 Hz), 1.09 (m, 2H), 1.34 (m, 2H), 1.47 (m, 2H), 1.59 (m, 2H), 3.15 (t, 2H, J = 6.3 Hz), 3.43 (t, 2H, J = 6.9 Hz), 4.82 (s, 1H), 7.74 (dd, 1H, J$_1$ = 7.9 Hz, J$_2$ = 1.6 Hz), 7.84 (d, 1H, J = 8.0 Hz), 8.06 (d, 1H, J = 1.4 Hz); MS (m/z): 303 [M + H] |
| 24 | N-ethyl-4-ethynyl-3-nitrobenzamide | I-17 | ¹HNMR (400 MHz, DMSO-d$_6$): δ 1.12 (t, 3H, J = 7.2 Hz), 3.30 (m, 2H), 4.84 (s, 1H), 7.85 (d, 1H, J = 8.0 Hz), 8.14 (dd, 1H, J$_1$ = 8.1 Hz, J$_2$ = 1.7 Hz), 8.51 (d, 1H, J = 1.6 Hz), 8.81 (t, 1H, J = 5.2 Hz); MS (m/z): 217 [M − H] |
| 25 | N-propyl-4-ethynyl-3-nitrobenzamide | I-18 | ¹HNMR (400 MHz, DMSO-d$_6$): δ 0.93 (t, 3H, J = 7.4 Hz), 1.59 (m, 2H), 3.27 (m, 2H), 4.90 (s, 1H), 7.92 (d, 1H, J = 8.1 Hz), 8.20 (dd, 1H, J$_1$ = 8.1 Hz, J$_2$ = 1.7 Hz), 8.57 (d, 1H, J = 1.6 Hz), 8.86 (t, 1H, J = 5.4 Hz); MS (m/z): 231 [M − H] |

-continued

| Example | Name | Structure | $^1$H NMR and MS (m/z) |
|---|---|---|---|
| 26 | N-butyl-4-ethynyl-3-nitrobenzamide | I-19 | $^1$HNMR (400 MHz, DMSO-d$_6$): δ 0.92 (t, 3H, J= 7.3 Hz), 1.36 (m, 2H), 1.56 (m, 2H), 3.30 (m, 2H), 4.90 (s, 1H), 7.91 (d, 1H, J = 8.0 Hz), 8.19 (dd, 1H, J$_1$ = 8.1 Hz, J$_2$ = 1.6 Hz), 8.56 (d, 1H, J = 1.5 Hz), 8.83 (t, 1H, J = 5.2 Hz); MS (m/z): 245 [M − H] |
| 27 | (4-ethynyl-3-nitrophenyl)-(pyrrolidin-1-yl)ketone | I-20 | $^1$HNMR (400 MHz, DMSO-d$_6$): δ 1.85 (m, 4H), 3.42 (m, 4H), 4.76 (s, 1H), 7.84 (d, 1H, J = 8.0 Hz), 7.86 (dd, 1H, J$_1$ = 8.0 Hz, J$_2$ = 1.5 Hz), 8.18 (d, 1H, J = 1.3 Hz); MS (m/z): 245 [M + H] |
| 28 | (4-ethynyl-3-nitrophenyl)-(piperidin-1-yl)ketone | I-21 | $^1$HNMR (400 MHz, DMSO-d$_6$): δ 1.61 (m, 6H), 3.28 (br s, 2H), 3.60 (br s, 2H), 4.83 (s, 1H), 7.76 (dd, 1H, J$_1$ = 8.0 Hz, J$_2$ = 1.6 Hz), 7.84 (d, 1H, J = 7.9 Hz), 8.10 (d, 1H, J = 1.5 Hz); MS (m/z): 259 [M + H] |
| 29 | (4-ethynyl-3-nitrophenyl)-(morpholin-4-yl)ketone | I-22 | $^1$HNMR (400 MHz, DMSO-d$_6$): δ 3.62 (m, 8H), 4.71 (s, 1H), 7.77 (dd, 1H, J$_1$ = 8.0 Hz, J$_2$ = 1.6 Hz), 7.82 (d, 1H, J = 7.9 Hz), 8.12 (d, 1H, J = 1.4 Hz); MS (m/z): 261 [M + H] |

-continued

| Example | Name | Structure | ¹H NMR and MS (m/z) |
|---|---|---|---|
| 30 | (4-ethynyl-3-nitrophenyl)-(piperazin-1-yl)ketone | I-23 | ¹HNMR (400 MHz, DMSO-$d_6$): δ 3.14 (br s, 4H), 3.57 (br s, 2H), 3.85 (br s, 2H), 4.89 (s, 1H), 7.84 (dd, 1H, $J_1$ = 8.0 Hz, $J_2$ = 1.5 Hz), 7.86 (d, 1H, J = 8.0 Hz), 8.22 (d, 1H, J = 1.3 Hz), 9.64 (s, 1H); MS (m/z): 260 [M + H] |
| 31 | (4-ethynyl-3-nitrophenyl)-(4-methylpiperazin-1-yl)-ketone | I-24 | ¹HNMR (400 MHz, DMSO-$d_6$): δ 2.20 (s, 3H), 2.28 (br s, 2H), 2.38 (br s, 2H), 3.33 (br s, 2H), 3.64 (br s, 2H), 4.84 (s, 1H), 7.76 (dd, 1H, $J_1$ = 8.0 Hz, $J_2$ = 1.3 Hz), 7.85 (d, 1H, J = 8.0 Hz), 8.11 (d, 1H, J = 1.2 Hz); MS (m/z): 274 [M + H] |
| 32 | (4-ethynyl-3-nitrophenyl)-(azetidinon-1-yl)ketone | I-25 | ¹HNMR (400 MHz, DMSO-$d_6$): δ 2.28 (m, 2H), 4.08 (t, 2H, J = 7.7 Hz), 4.35 (t, 2H, J = 7.6 Hz), 4.90 (s, 1H), 7.86 (d, 1H, J = 8.0 Hz), 7.93 (dd, 1H, $J_1$ = 8.0 Hz, $J_2$ = 1.6 Hz), 8.24 (d, 1H, J = 1.5 Hz); MS (m/z): 231 [M + H] |
| 33 | N-methyl-4-(1-propynyl)-3-nitrobenzamide | I-26 | ¹HNMR (400 MHz, DMSO-$d_6$): δ 2.14 (s, 3H), 2.79 (d, 3H, J = 4.5 Hz), 7.74 (d, 1H, J = 8.1 Hz), 8.08 (dd, 1H, $J_1$ = 8.1 Hz, $J_2$ = 1.6 Hz), 8.45 (d, 1H, J = 1.6 Hz), 8.76 (m, 1H); MS (m/z): 219 [M + H] |

Example 34

Preparation of N-methyl-4-cyano-3-nitrobenzamide (Compound I-27)

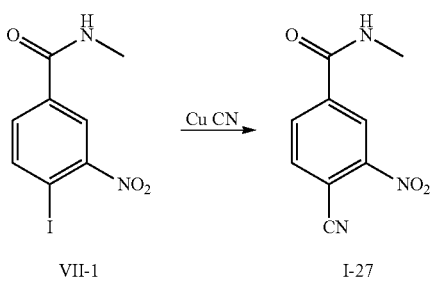

2 g (6.53 mmol) N-methyl-4-iodo-3-nitrobenzamide (Compound VII-1), 0.09 g (10.0 mmol) cuprous cyanide and 10 ml hexamethylphosphoric triamide were added into a reaction flask. The mixture was heated to 100° C. and reacted for 40 minutes, and after completing the reaction, the mixture was cooled to room temperature, and then extracted with ethyl acetate. The organic layer was washed with water for three times, dried over anhydrous sodium sulfate, decolorized with activated charcoal, filtered, and the filtrate was concentrated to dryness, recrystallized from ethyl acetate to obtain 0.74 g N-methyl-4-cyano-3-nitrobenzamide (Compound I-27), yield 55.2%.

$^1$HNMR (400 MHz, DMSO-$d_6$): δ 2.84 (d, 3H, J=4.6 Hz), 8.27 (d, 1H, J=8.0 Hz), 8.32 (dd, 1H, $J_1$=8.0 Hz, $J_2$=1.5 Hz), 8.72 (d, 1H, J=1.4 Hz), 8.90 (m, 1H); MS (m/z): 204 [M–H].

Example 35

Preparation of 4-ethynyl-3-nitrosobenzamide (Compound I-28)

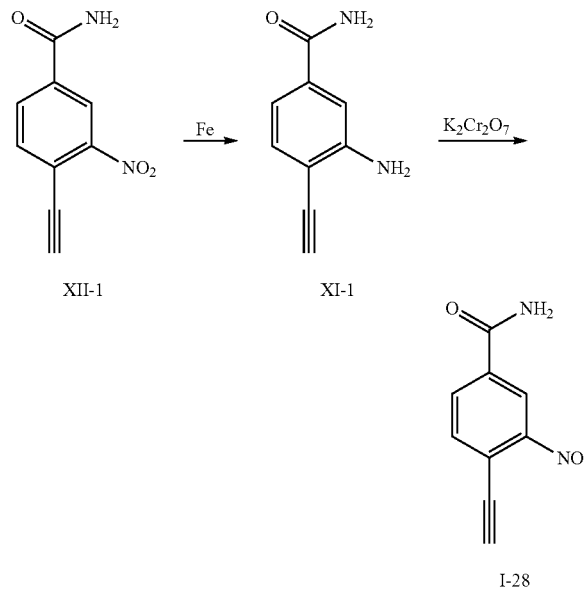

Step 1: 5 g (26.3 mmol) 4-Ethynyl-3-nitrobenzamide (Compound XII-1) and 75 ml tetrahydrofuran were added into a 150 ml four-necked flask, mechanically stirred to dissolve, and added with 10 ml aqueous solution of 10 g (186.9 mmol) ammonium chloride, then 10 g (178.5 mmol) iron powder was added portionwise and reacted at room temperature for 4 hours until the reaction was completed. The mixture was filtrated, and the filter cake was washed with tetrahydrofuran. The filtrate was extracted with ethyl acetate and the organic phase was washed with water, dried over anhydrous sodium sulfate, decolorized with activated charcoal, filtered, and concentrated to precipitate a solid, which was filtrated and dried to obtain 4-ethynyl-3-aminobenzamide (Compound XI-1, gray solid), 2.4 g, yield 59.4%.

$^1$HNMR (400 MHz, DMSO-$d_6$): δ 4.55 (s, 1H), 7.25 (dd, 1H, $J_1$=8.0 Hz, $J_2$=1.6 Hz), 7.31 (d, 1H, J=7.9 Hz), 7.35 (s, 1H), 7.61 (d, 1H, J=1.4 Hz), 7.97 (s, 1H), 8.21 (s, 1H), 8.65 (s, 1H); MS (m/z): 161 [M+H].

Step 2: 0.46 g (2.87 mmol) 4-ethynyl-3-aminobenzamide (Compound XI-1), 10 ml water, were added into a 50 ml single-neck flask, then 1.2 g 58% sulfuric acid was added, and then 0.92 g 18.5% potassium dichromate solution. The mixture was stirred for 3 minutes until completing the reaction, extracted with ethyl acetate, dried over anhydrous sodium sulfate, and separated by column chromatography to obtain 0.06 g 4-ethynyl-3-nitrosobenzamide (Compound I-28, yellow-green solid), yield 12%, stored at −20° C.

$^1$HNMR (400 MHz, DMSO-$d_6$): δ 4.97 (s, 1H), 6.99 (d, 1H, 1.3 Hz), 7.70 (s, 1H), 8.09 (d, 1H, J=8.0 Hz), 8.27 (s, 1H), 8.34 (dd, 1H, $J_1$=8.0 Hz, $J_2$=1.6 Hz); MS (m/z): 219 [M+HCOO$^-$].

Example 36

Preparation of (4-ethynyl-3-nitrophenyl)(4-methylpiperazin-1-yl)ketone hydrochloride (Compound I-29)

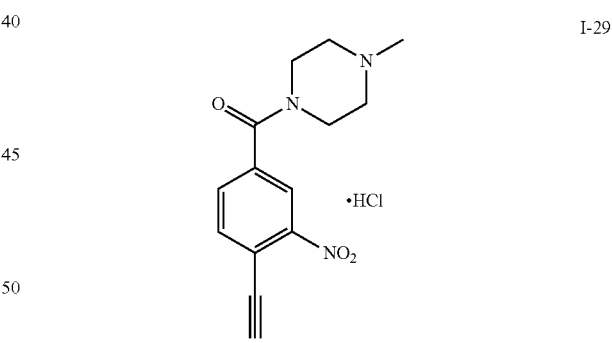

0.75 g (2.74 mmol) (4-ethynyl-3-nitrophenyl) (4-methylpiperazin-1-yl)ketone (Compound I-24) and 7.5 ml anhydrous methanol were added into a 50 ml single-neck flask, magnetically stirred to dissolve. The mixture was adjusted to a pH value of 2 by adding concentrated hydrochloric acid. A white solid was precipitated under cooling with ice water, and filtered. The filter cake was washed with anhydrous ethanol, dried to obtain 0.46 g (4-ethynyl-3-nitrophenyl) (4-methylpiperazin-1-yl)ketone hydrochloride (Compound I-29), yield: 54.1%.

$^1$HNMR (400 MHz, DMSO-$d_6$): δ 2.76 (s, 3H), 3.16 (br s, 4H), 3.66 (br s, 4H), 4.91 (s, 1H), 7.85 (dd, 1H, $J_1$=8.0 Hz, $J_2$=1.4 Hz), 7.88 (d, 1H, J=8.0 Hz), 8.21 (d, 1H, J=1.3 Hz); MS (m/z): 274 [M+H—HCl]

Example 37

Preparation of (4-ethynyl-3-nitrophenyl)(piperazin-1-yl)ketone hydrochloride (Compound I-30)

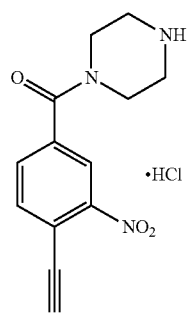

(4-ethynyl-3-nitrophenyl)(piperazin-1-yl)ketone hydrochloride (Compound I-30) was prepared according to the method of Example 36, using (4-ethynyl-3-nitrophenyl)(piperazin-1-yl)ketone (Compound I-23) as starting material.

$^1$HNMR (400 MHz, D$_2$O): δ 3.32 (br s, 2H), 3.45 (br s, 2H), 3.78 (br s, 2H), 4.03 (br s, 2H), 4.11 (s, 1H), 7.80 (dd, 1H, J$_1$=8.0 Hz, J$_2$=1.6 Hz), 7.91 (d, 1H, J=8.0 Hz), 8.24 (d, 1H, J=1.4 Hz); MS (m/z): 260 [M+H—HCl]

Pharmacodynamic screening of the compounds according to the present invention is performed in the following manner I. Pharmacodynamic Screening In Vitro 1. Cell Culture Human colon cancer cell strains (Colo205 and HCT-116), human breast cancer cell strains (MCF-7 and MDA-MB435), human lung cancer cell strains (A549, 95D and NCI460), human ovarian cancer cell strains (OVCAR-5, OVCAR-8, HO8910 and SKOV-3), human leukemia (HL-60 and K562), human prostate cancer (DU145 and BXPC-3), human uterine cancer (Hela), human pancreatic cancer (PANC-1), human hepatoma (HepG 2) were all obtained from ATCC. Colo205, HL-60, K562 cells were cultured in RPMI 1640 containing 2 mM/L glutamine, 10% FBS, 1.0 mM sodium pyruvate. HCT-116, MCF-7, A549, 95D, HO8910, NCI460, OVCAR-5, OVCAR-8, DU145, BXPC-3, Hela, PANC-1, HepG2 cells were cultured in DMEM containing 2 mM/L glutamine, 10% FBS. MDA-MB435 cells were cultured in L-15 containing 2 mM/L glutamine, 10% FBS. SKOV-3 cells were cultured in McCoy's containing 2 mM/L glutamine, 10% FBS. Colo205, HL-60 and K562 cells were seeded in 96-well plates, 150 μL/well and 8000 cells/well, and the 96-well plates were pre-incubated in an incubator at 37° C. with 5% CO$_2$, 100% relative humidity for 24 hours. HCT-116, MCF-7, NCI460, OVCAR-5, OVCAR-8, Hela, HepG 2 and MDA-MB435 cells were seeded in 96-well plates, 5000 cells/well; A549, 95D, HO8910, DU145, BXPC-3, PANC-1 and SKOV-3 cells were seeded in 96-well plates, 10000 cells/well, and the 96-well plates were pre-incubated in an incubator at 37° C. with 5% CO$_2$, 100% relative humidity for 24 hours, to allow the cells to adhere.

2. Compounds Screening

50 μL of pre-cooled 50% (mass/volume) TCA was added into the time zero control wells for each cell strain to fix the cells. To other wells, 50 μL of various concentrations of compounds were added, and maintained for 48 h, wherein each drug concentration was in triplicate, and there were blank control wells (cell culture medium without cells), drug-free control wells (with no drugs but the same volume of complete medium) and positive drug BSI-201 control wells, and the plates were incubated in an incubator at 37° C. with 5% CO$_2$, full humidity (100% relative humidity) for 48 hours 3. Cell Detection 50 μL pre-cooled 50% (mass/volume) TCA was added onto the surface of the culture medium to fix the cells, which was then placed at 4° C. for 1 h. The supernatant was removed and each well was washed with deionized water for 5 times to remove TCA, serum proteins, etc. After dried in the air, about 100 μL enough amount of 0.4% SRB (formulated with 1% acetic acid) was added into each well, and was placed at room temperature for 20 to 30 min. Liquid in each well was discarded and each well was rapidly washed with 1% acetic acid for five times, to remove unbound dye until the unbound dye was completely rinsed clean. After dried in the air until the moisture was invisible, each well was added 200 μL Tris base to dissolve, shaken on a plate oscillator for 5 min or mixed by beating up and down with a pipette tip, and then measured on the multi-function instruction (M5 Detection System, MD Group Ltd.) with a detection wavelength of 515 nm, zero adjusted with 690 nm blank control.

The dose-response curve was plotted by XL-fit to determine the GI$_{50}$ value.

4. Screening Results

Through screening experiments for in vitro efficacy using BSI-201 (Iniparib) as positive drug, the results showed that compounds I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, and I-30 have inhibitory effects on tumor cell proliferation, wherein the efficacy of Compound I-1 is 10 times higher than that of the positive drug BSI-201 in the measured 18 tumor cell strains; the efficacies of I-2, I-3, I-14, I-15, I-17, I-20, I-21, I-23, I-24, I-29, and I-30 are slightly lower than that of I-1; I-4, I-5, I-6, I-7, I-8, I-9, I-10, I-11, I-12, I-13, I-16, I-18, I-19, I-25, I-27, and I-28 also have good effects on inhibition of tumor cell proliferation. The screening results are shown in Table 1.

TABLE 1

Part of the data for the inhibitory activity of compound (I) on tumor cells

| Tumor cell strain | BSI-201 | I-1 | I-2 | I-3 | I-4 | I-5 | I-6 | I-7 | I-8 | I-9 | I-10 | I-11 | I-12 | I-13 | I-14 | I-15 |
|---|---|---|---|---|---|---|---|---|---|---|---|---|---|---|---|---|
| | | | | | | | | | | | | | | | | |
| | | | | | | | GI$_{50}$ (μm) | | | | | | | | | |
| HCT-116 | 64.684 | 1.904 | — | 5.602 | — | 17.913 | — | — | 12.973 | 22.487 | 18.267 | 12.135 | — | — | 11.213 | 11.951 |
| MDA-MB435 | 64.398 | 2.054 | 11.713 | 4.155 | 12.559 | — | — | 9.667 | 32.154 | — | — | — | — | 6.244 | 1.008 | — |
| HL-60 | 74.115 | 2.111 | 2.022 | 3.196 | — | — | — | — | — | 9.707 | 3.778 | 2.355 | 34.583 | — | 1.993 | — |
| PANC-1 | 25.526 | 7.406 | 13.720 | 2.482 | — | — | 9.087 | 3.149 | — | — | — | — | — | — | 19.916 | — |
| Colo 205 | 75.958 | 4.839 | 7.026 | 4.319 | — | — | — | — | — | — | — | — | — | — | 2.786 | — |
| SKOV-3 | 38.511 | 3.174 | 3.813 | 15.035 | — | — | — | — | — | — | — | — | — | — | 10.284 | — |
| HepG 2 | >100 | 8.733 | 11.301 | 12.024 | — | — | — | — | — | — | — | — | — | — | 4.27 | — |
| MCF-7 | 40.092 | 2.466 | 2.081 | 6.812 | — | 10.114 | — | — | — | 6.697 | 12.254 | 10.700 | — | 25.254 | 20.147 | 9.916 |
| A549 | 104.53 | 4.563 | 8.036 | 24.985 | — | — | — | — | — | — | — | — | — | — | 17.622 | — |
| BXPC-3 | 105.01 | 4.678 | 7.421 | 7.504 | — | — | — | — | — | — | — | — | — | — | 4.896 | — |
| OVCAR-5 | 61.065 | 4.290 | 4.236 | — | — | — | — | — | — | — | — | — | — | — | 20.897 | — |
| K562 | 44.607 | 3.021 | 2.796 | 7.033 | — | — | 20.191 | 10.082 | — | — | — | — | — | — | 4.524 | 2.369 |
| DU145 | 86.647 | 4.78 | 3.307 | 3.788 | — | — | — | — | — | — | — | — | — | — | 4.172 | — |
| 95D | 53.824 | 1.88 | 3.625 | 4.379 | — | — | — | — | — | — | — | — | — | — | 16.793 | — |
| OVCAR-8 | 102.551 | 11.735 | 14.126 | 16.311 | — | — | — | — | — | — | — | — | — | — | 3.635 | — |
| HO8910 | 72.563 | 1.471 | 3.435 | 4.025 | — | — | — | — | — | — | — | — | — | — | 5.000 | — |
| NCI-460 | >100 | 10.878 | 33.751 | 37.349 | — | 20.096 | — | — | — | 11.474 | 24.092 | 13.449 | — | — | 20.883 | 16.988 |
| Hela | 64.718 | 5.276 | 7.104 | 9.901 | — | — | — | — | — | — | — | — | — | — | 6.704 | — |

| Tumor cell strain | BSI-201 | I-16 | I-17 | I-18 | I-19 | I-20 | I-21 | I-22 | I-23 | I-24 | I-25 | I-26 | I-27 | I-28 | I-29 | I-30 |
|---|---|---|---|---|---|---|---|---|---|---|---|---|---|---|---|---|
| | | | | | | | | GI$_{50}$ (μm) | | | | | | | | | |
| HCT-116 | 64.684 | 12.928 | 5.059 | 9.451 | 9.007 | 9.987 | 8.443 | — | 12.397 | 8.623 | 10.922 | — | — | — | 14.269 | 10.260 |
| MDA-MB435 | 64.398 | — | 2.759 | — | — | 8.490 | 5.861 | 6.527 | — | 14.518 | — | ND | 29.266 | — | 8.440 | 3.058 |
| HL-60 | 74.115 | 1.265 | 2.621 | 4.860 | 5.152 | 2.238 | 2.869 | — | 12.325 | 2.467 | — | — | — | — | — | 9.267 |
| PANC-1 | 25.526 | — | 12.392 | — | — | 7.644 | 12.519 | — | 23.796 | 24.326 | — | — | — | — | — | 18.123 |
| Colo 205 | 75.958 | — | 3.208 | — | — | 2.607 | 1.521 | — | — | 10.865 | — | — | — | — | — | — |
| SKOV-3 | 38.511 | — | 8.400 | — | — | 9.908 | 22.472 | — | 31.267 | 9.766 | — | 105.222 | — | — | — | — |
| HepG 2 | >100 | — | 5.849 | — | — | 5.541 | 15.951 | — | — | 7.121 | — | — | — | — | — | — |
| MCF-7 | 40.092 | 8.208 | 10.633 | 6.291 | 9.592 | 20.610 | 16.053 | 13.415 | 9.238 | 21.542 | 9.495 | ND | 31.58 | 9.776 | 11.753 | 5.971 |
| A549 | 104.53 | — | 12.185 | — | — | 17.271 | 17.859 | — | 56.788 | 30.099 | — | 129.849 | — | — | — | — |
| BXPC-3 | 105.01 | — | 4.786 | — | — | 3.355 | 3.909 | — | — | 10.184 | — | — | — | — | — | — |
| OVCAR-5 | 61.065 | — | 16.063 | — | — | 20.293 | 17.460 | — | — | 35.564 | — | — | — | — | — | — |
| K562 | 44.607 | — | 2.590 | — | — | 4.349 | 1.770 | — | 16.172 | 8.027 | — | — | — | — | — | 15.286 |
| DU145 | 86.647 | — | 2.993 | — | — | 4.992 | 2.236 | — | 3.444 | 6.168 | — | — | — | — | — | 5.839 |
| 95D | 53.824 | — | 10.262 | — | — | 15.055 | 14.535 | — | 10.866 | 25.754 | — | — | — | 18.067 | 15.841 | 10.945 |
| OVCAR-8 | 102.551 | — | 4.601 | — | — | 4.008 | 1.635 | — | — | 8.916 | 14.402 | — | — | 17.216 | 29.275 | 10.287 |
| HO8910 | 72.563 | — | 3.338 | — | — | 4.853 | 4.337 | — | — | 10.243 | — | — | — | — | — | — |
| NCI-460 | >100 | 15.506 | 14.009 | 7.093 | 10.127 | 19.909 | 5.861 | — | 25.643 | 31.072 | 27.705 | — | — | — | 28.171 | 19.455 |
| Hela | 64.718 | — | 4.428 | — | — | 8.984 | 4.165 | — | 11.191 | 10.122 | — | — | — | — | — | 13.962 |

Note:
In Table 1, "—" indicates that the activity was not tested; "ND" indicates that the compound is active, but its GI$_{50}$ value could not be detected under the test condition employed.

II. Pharmacodynamic Screening In Vivo

1. Establishment of Animal Model 5-6 week old female or male BALB/C nude mice, about 18-20 g in weight, were raised. Human cancer xenograft tumor model in nude mouse was established by the following steps: human colon cancer cell strains HCT-116 and Colo205, human breast cancer cell strain MDA-MB435, human prostate cancer cell strain BXPC-3, human ovarian cancer cell strain SKOV-3, human lung cancer cell strain A549, human pancreatic cancer cell strain PANC-1, and human uterine cancer cell strain Hela were all obtained from ATCC. Each cell strain was cultured, and monolayer of cultured tumor cells were digested off the walls, collected and resuspended in serum-free culture medium, and adjusted to a concentration of $2\times10^6/0.2$ mL, which was then brought to the animal room in an ice box. 0.2 mL cell suspension was drawn directly by a syringe with 6-gauge needle and subcutaneously transplanted into the scapula part of the rear part of nude mouse's left armpit, $2\times10^6/0.2$ mL for each mouse, and the tumor volume was measured every 2-3 days. After two weeks, tumor was removed under sterile conditions from tumor-bearing nude mice with vigorous tumor growth and without diabrosis. The tumor tissue was cut into pieces of about 2~3 mm and inoculated subcutaneously into the scapula part of the rear part of nude mouse's left armpit. After three passages, when the tumor volume reached 100 mm³, the nude mice with too large or too small tumors were eliminated and the rest were randomly divided into groups for the administration.

2. Compound Screening

The mice were randomly divided into 5 groups, including negative control group (solvent), positive control group (BSI-201, 80 mg/kg), and three treatment groups with high, middle and low doses (40 mg/kg, 30 mg/kg, and 20 mg/kg respectively, wherein the high dose was below the MTD), and there were 8 nude mice in each group except that there are 16 ones in the negative control group. They were administered by intraperitoneal injection once a day for 3 consecutive weeks, during which body weight and tumor volume of the animals were detected and the death number of animals was recorded every 2 days. The animals were sacrificed 24 hours after the last administration, and the volume sizes of tumor, tumor weight, and body weight of nude mice were measured; growth curves of tumor volume, growth curves of body weight of nude mice and tumor inhibition rate, animal mortality were plotted, and relative tumor proliferation rate T/C (%) was calculated according to the equation T/C (%)=TRTV/CRTV*100%. (TRTV: RTV of the treatment group; CRTV: RTV of the negative control group, relative tumor volume RTV=$V_t/V_0$, wherein $V_0$ is the tumor volume when the mice were divided into groups for administration, $V_t$ is the tumor volume after the administration).

3. Screening Results

Through pharmacodynamic screening experiments for in vivo efficacy, using BSI-201 (Iniparib) as positive drug, the results showed that a dose of 30 mg/kg Compounds I-1 had equivalent efficacy to that of 80 mg/kg BSI-201 and had significant pharmacodynamic effect. The screening results are shown in Table 2.

TABLE 2

Tumor inhibitory rate of Compound (I) on the tumor model in nude mouse

| | Cell strain | I-1 | BSI-201 |
|---|---|---|---|
| Relative tumor proliferation rate T/C (%) of Compound I-1 in each type of tumor model | HCT-116 | 52%(30, 21) | 54%(80, 21) |
| | Colo-205 | 42%(30, 21) | 50%(80, 21) |
| | MDA-MB-435 | 40%(30, 21) | 44%(80, 21) |
| | BXPC-3 | 43%(30, 22) | 48%(80, 22) |
| | SKOV-3 | 45%(30, 21) | 41%(80, 21) |
| | A549 | 40%(30, 21) | 42%(80, 21) |
| | Hela | 50%(30, 21) | 48%(80, 21) |
| | PANC-1 | 40%(30, 21) | 45%(80, 21) |

Note:
The values in parentheses represent dose and time for the administration (mg/kg, time for the administration (d)). For each model, when T/C (%) < 60%, it can be determined that the compound is effective to the model; the mode for all the administrations is intraperitoneal injection. The solvent was 10% Solutal.

All literatures mentioned in the present invention are cited in the present application as references, just as each literature is individually cited as a reference. It should also be understood that after reading the above described contents of the present invention, a skilled in the art can make various changes or modifications to the present invention, and these equivalents also fall within the scope as defined by the appended claims of the present application.

The invention claimed is:

1. A compound represented by formula (I),

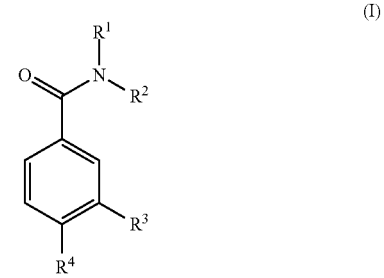

(I)

or a pharmaceutically acceptable salt thereof,
wherein
$R^1$ and $R^2$ are independently selected from the group consisting of hydrogen, substituted or unsubstituted ($C_1$-$C_8$) alkyl, substituted or unsubstituted ($C_3$-$C_8$)alkenyl, substituted or unsubstituted ($C_3$-$C_8$)alkynyl, substituted or unsubstituted ($C_3$-$C_7$)cycloalkyl, —$COR^5$, and —$CO_2R^6$; or $R^1$ and $R^2$ can also cyclize to form a substituted or unsubstituted 4-, 5-, or 6-membered ring;
$R^3$ is nitro or nitroso;
$R^4$ is selected from the group consisting of ethynyl, propynyl, and cyano;
$R^5$ is selected from the group consisting of substituted or unsubstituted ($C_1$-$C_8$)alkyl, substituted or unsubstituted ($C_3$-$C_8$)alkenyl, substituted or unsubstituted ($C_3$-$C_8$) alkynyl, substituted or unsubstituted ($C_3$-$C_7$)cycloalkyl, and substituted or unsubstituted aryl;
$R^6$ is selected from the group consisting of substituted or unsubstituted ($C_1$-$C_8$)alkyl, substituted or unsubstituted ($C_3$-$C_8$)alkenyl, substituted or unsubstituted ($C_3$-$C_8$) alkynyl, and substituted or unsubstituted ($C_3$-$C_7$)cycloalkyl.

2. The compound according to claim 1, wherein $R^1$ and $R^2$ are independently selected from the group consisting of hydrogen, substituted or unsubstituted ($C_1$-$C_8$)alkyl, —$COR^5$ or —$CO_2R^6$, and $R^1$ and $R^2$ can also cyclize to form a substituted or unsubstituted 4-, 5-, or 6-membered ring, wherein $R^5$ is a substituted or unsubstituted ($C_1$-$C_8$)alkyl, a substituted or unsubstituted ($C_3$-$C_8$)alkenyl, a substituted or unsubstituted ($C_3$-$C_8$)alkynyl, a substituted or unsubstituted ($C_3$-$C_7$)cycloalkyl, and a substituted or unsubstituted aryl; $R^6$ is a substituted or unsubstituted ($C_1$-$C_8$)alkyl, a substituted or unsubstituted ($C_3$-$C_8$)alkenyl, a substituted or unsubstituted ($C_3$-$C_8$)alkynyl, and a substituted or unsubstituted ($C_3$-$C_7$) cycloalkyl.

3. The compound according to claim 2, wherein $R^1$ and $R^2$ are independently selected from the group consisting of hydrogen, substituted or unsubstituted ($C_1$-$C_8$)alkyl, —$COR^5$ or —$CO_2R^6$, and $R^1$ and $R^2$ can also cyclize to form a substituted or unsubstituted 4-, 5-, or 6-membered ring, wherein $R^5$ is a substituted or unsubstituted ($C_1$-$C_8$)alkyl, a substituted or unsubstituted ($C_3$-$C_7$)cycloalkyl, a substituted or unsubstituted aryl; $R^6$ is a substituted or unsubstituted ($C_1$-$C_8$)alkyl, a substituted or unsubstituted ($C_3$-$C_7$)cycloalkyl.

4. The compound according to claim 3, wherein $R^1$ and $R^2$ are independently selected from the group consisting of hydrogen, methyl, ethyl, and propyl.

5. The compound according to claim 3, wherein $R^1$ and $R^2$ cyclize to form a substituted or unsubstituted 5- or 6-membered ring.

6. The compound according to claim 5, wherein $R^1$ and $R^2$ cyclize to form a substituted or unsubstituted 5- or 6-membered ring containing one or more heteroatoms selected from nitrogen, oxygen and sulfur.

7. The compound according to claim 1, wherein $R^5$ is substituted or unsubstituted ($C_1$-$C_8$)alkyl.

8. The compound according to claim 1, wherein $R^5$ is substituted or unsubstituted aryl.

9. The compound according to claim 1, wherein $R^6$ is substituted or unsubstituted ($C_1$-$C_8$)alkyl.

10. The compound according to claim 9, wherein $R^6$ is selected from the group consisting of methyl, ethyl, n-propyl, isopropyl, n-butyl, and isobutyl.

11. The compound according to claim 1, wherein $R^3$ is nitro.

12. The compound according to claim 1, wherein $R^4$ is ethynyl or propynyl.

13. The compound according to claim 1, wherein $R^4$ is cyano.

14. The compound according to claim 1, wherein the compound of formula (I) is selected from the group consisting of
4-ethynyl-3-nitrobenzamide (I-1),
N-methoxycarbonyl-4-ethynyl-3-nitrobenzamide (I-2),
N-ethoxycarbonyl-4-ethynyl-3-nitrobenzamide (I-3),
N-propoxycarbonyl-4-ethynyl-3-nitrobenzamide (I-4),
N-butoxycarbonyl-4-ethynyl-3-nitrobenzamide (I-5),
N-isopropoxycarbonyl-4-ethynyl-3-nitrobenzamide (I-6),
N-isobutoxycarbonyl-4-ethynyl-3-nitrobenzamide (I-7),
4-cyano-3-nitrobenzamide (I-8),
N-methyl-4-ethynyl-3-nitrobenzamide (I-9),
N,N-dimethyl-4-ethynyl-3-nitrobenzamide (I-10),
N-acetyl-4-ethynyl-3-nitrobenzamide (I-11),
4-(1-propynyl)-3-nitrobenzamide (I-12),
N-benzoyl-4-ethynyl-3-nitrobenzamide (I-13),
N,N-diethyl-4-ethynyl-3-nitrobenzamide (I-14),
N,N-dipropyl-4-ethynyl-3-nitrobenzamide (I-15),
N,N-dibutyl-4-ethynyl-3-nitrobenzamide (I-16),
N-ethyl-4-ethynyl-3-nitrobenzamide (I-17),
N-propyl-4-ethynyl-3-nitrobenzamide (I-18),
N-butyl-4-ethynyl-3-nitrobenzamide (I-19),
(4-ethynyl-3-nitrophenyl)(pyrrolidin-1-yl)ketone (I-20),
(4-ethynyl-3-nitrophenyl)(piperidin-1-yl)ketone (I-21),
(4-ethynyl-3-nitrophenyl)(morpholin-4-yl)ketone (I-22),
(4-ethynyl-3-nitrophenyl)(piperazin-1-yl)ketone (I-23),
(4-ethynyl-3-nitrophenyl)(4-methylpiperazin-1-yl)ketone (I-24),
(4-ethynyl-3-nitrophenyl)(azetidinon-1-yl)ketone (I-25),
N-methyl-4-(1-propynyl)-3-nitrobenzamide (I-26),
N-methyl-4-cyano-3-nitrobenzamide (I-27),
4-ethynyl-3-nitrosobenzamide (I-28),
(4-ethynyl-3-nitrophenyl)(4-methylpiperazin-1-yl)ketone hydrochloride (I-29), and
(4-ethynyl-3-nitrophenyl)(piperazin-1-yl)ketone hydrochloride (I-30).

15. A method for preparing the compound of formula (I) according to claim 1, comprising reacting the compound represented by formula (II) with the compound represented by formula (X) to obtain the compound of formula (I):

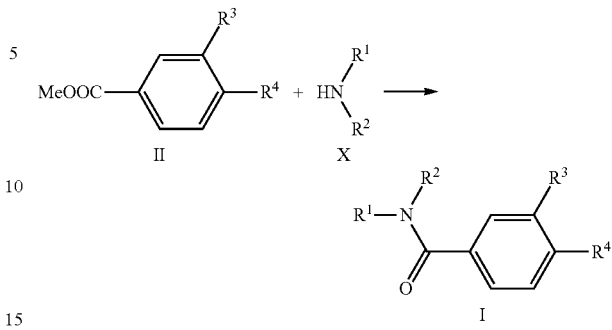

wherein, $R^1$ and $R^2$ are hydrogen, $R^3$ is nitro, and $R^4$ is ethynyl, propynyl, or cyano.

16. A method for preparing the compound of formula (I) according to claim 1, comprising reacting the compound represented by formula (IX) with $(R^5CO)_2O$, $R^5COX$, or $XCO_2R^6$ to obtain the compound of formula (I):

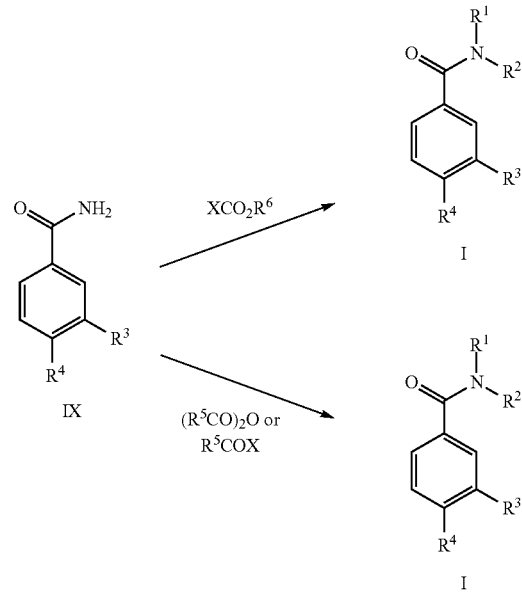

wherein, $R^1$ is hydrogen, $R^2$ is —$COR^5$ or —$CO_2R^6$, $R^3$ is nitro, $R^4$ is ethynyl, propynyl, or cyano, $R^5$ and $R^6$ are as defined in claim 1, and X is halogen.

17. A method for preparing the compound of formula (I) according to claim 1, comprising desilylation of the compound represented by formula (VIII) to obtain the compound of formula (I):

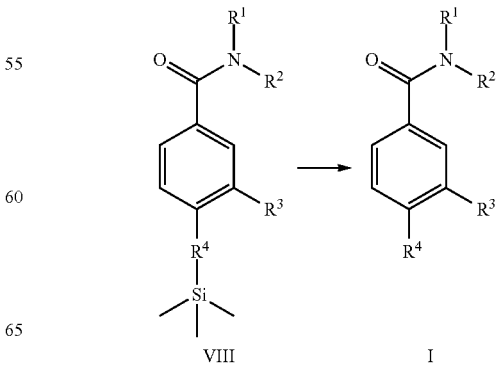

wherein, $R^1$ and $R^2$ are independently selected from the group consisting of hydrogen, substituted or unsubstituted $(C_1\text{-}C_8)$alkyl, substituted or unsubstituted $(C_3\text{-}C_8)$alkenyl, substituted or unsubstituted $(C_3\text{-}C_8)$alkynyl, and substituted or unsubstituted $(C_3\text{-}C_7)$cycloalkyl, or $R^1$ and $R^2$ can also cyclize to form a substituted or unsubstituted 4-, 5-, or 6-membered ring, but $R^1$ and $R^2$ cannot be hydrogen at the same time; $R^3$ is nitro, and $R^4$ is ethynyl or propynyl.

18. A method for preparing the compound of formula (I) according to claim 1:

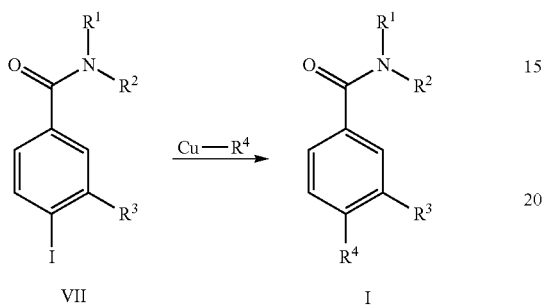

wherein, $R^1$ and $R^2$ are independently selected from the group consisting of hydrogen, substituted or unsubstituted $(C_1\text{-}C_8)$alkyl, substituted or unsubstituted $(C_3\text{-}C_8)$alkenyl, substituted or unsubstituted $(C_3\text{-}C_8)$alkynyl, and substituted or unsubstituted $(C_3\text{-}C_7)$cycloalkyl, or $R^1$ and $R^2$ can also cyclize to form a substituted or unsubstituted 4-, 5-, or 6-membered ring, but $R^1$ and $R^2$ cannot be hydrogen at the same time; $R^3$ is nitro, and $R^4$ is cyano.

19. A method for preparing the compound of formula (I) according to claim 1:

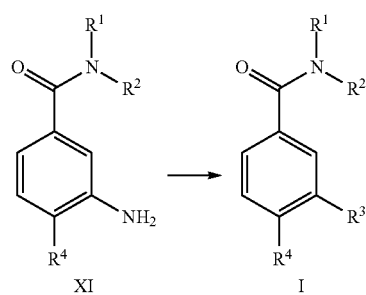

wherein, $R^1$ and $R^2$ are independently selected from the group consisting of hydrogen, substituted or unsubstituted $(C_1\text{-}C_8)$alkyl, substituted or unsubstituted $(C_3\text{-}C_8)$alkenyl, substituted or unsubstituted $(C_3\text{-}C_8)$alkynyl, substituted or unsubstituted $(C_3\text{-}C_7)$cycloalkyl, —$COR^5$ and —$CO_2R^6$; $R^1$ and $R^2$ can also cyclize to form a substituted or unsubstituted 4-, 5-, or 6-membered ring; $R^3$ is nitroso; $R^4$ is ethynyl, propynyl or cyano; $R^5$ is a substituted or unsubstituted $(C_1\text{-}C_8)$alkyl, a substituted or unsubstituted $(C_3\text{-}C_8)$alkenyl, a substituted or unsubstituted $(C_3\text{-}C_8)$alkynyl, a substituted or unsubstituted $(C_3\text{-}C_7)$cycloalkyl, and a substituted or unsubstituted aryl; $R^6$ is a substituted or unsubstituted $(C_1\text{-}C_8)$alkyl, a substituted or unsubstituted $(C_3\text{-}C_8)$alkenyl, a substituted or unsubstituted $(C_3\text{-}C_8)$alkynyl, and a substituted or unsubstituted $(C_3\text{-}C_7)$cycloalkyl.

20. A pharmaceutical composition, comprising an effective dose of the compound of formula (I) according to claim 1, or a pharmaceutically acceptable salt thereof.

21. A method for treating a disease associated with poly (ADP-ribose) polymerase (PARP) inhibitor by administering to a subject in need thereof a compound of claim 1, wherein the disease is selected from stroke, myocardial infarction, colon cancer, breast cancer, lung cancer, ovarian cancer, gastric cancer, acute leukemia, chronic leukemia, prostate cancer, human uterine cancer, pancreatic cancer, liver cancer, brain cancer, CNS tumor, bladder cancer, kidney cancer, skin cancer, neck cancer, myosarcoma, lymphoma, and bone cancer.

22. The compound according to claim 1, wherein, for the substituted or unsubstituted $(C_3\text{-}C_8)$alkenyl and the substituted or unsubstituted $(C_3\text{-}C_8)$alkynyl, the double bond of the alkenyl and the triple bond of the alkynyl are not directly connected to an amide nitrogen, a carbonyl or a carbonyloxy.

23. The compound according to claim 5, wherein the substituted or unsubstituted 5- or 6-membered ring contains one or more nitrogen atoms.

24. The compound according to claim 6, wherein the substituted or unsubstituted 5- or 6-membered ring is a pyrrolidine ring, piperidine ring, morpholine ring, or piperazine ring.

25. The compound according to claim 7, wherein $R^5$ is methyl.

26. The compound according to claim 8, wherein $R^5$ is phenyl.

27. The compound according to claim 10, wherein $R^6$ is methyl or ethyl.

28. The compound according to claim 11, wherein $R^3$ is nitro.

29. The compound according to claim 19, wherein $R^4$ is ethynyl.

* * * * *